(12) United States Patent
Rabb et al.

(10) Patent No.: US 10,610,133 B2
(45) Date of Patent: Apr. 7, 2020

(54) USING ACTIVE IR SENSOR TO MONITOR SLEEP

(71) Applicant: Google Inc., Mountain View, CA (US)

(72) Inventors: Laura Rabb, San Jose, CA (US); Andrea Colaco, Mountain View, CA (US); Michael Dixon, Sunnyvale, CA (US); Ghulam A. Kirmani, Mountain View, CA (US); Luis Villaran, East Palo Alto, CA (US); Kenneth Louis Herman, San Jose, CA (US); Bryan James, Menlo Park, CA (US); Casey Mills Davis, Palo Alto, CA (US); Yash Modi, San Mateo, CA (US)

(73) Assignee: Google LLC, Mountain View, CA (US)

( * ) Notice: Subject to any disclaimer, the term of this patent is extended or adjusted under 35 U.S.C. 154(b) by 669 days.

(21) Appl. No.: 14/933,069

(22) Filed: Nov. 5, 2015

(65) Prior Publication Data

US 2017/0127980 A1    May 11, 2017

(51) Int. Cl.
*A61B 5/11*     (2006.01)
*A61B 5/00*     (2006.01)
(Continued)

(52) U.S. Cl.
CPC .......... *A61B 5/1128* (2013.01); *A61B 5/0205* (2013.01); *A61B 5/02433* (2013.01);
(Continued)

(58) Field of Classification Search
CPC .......................... A61B 5/02433; A61B 5/4809
See application file for complete search history.

(56) References Cited

U.S. PATENT DOCUMENTS 6,081,269 A    6/2000 Quarendon
6,126,611 A * 10/2000 Bourgeois ............ A61N 1/3601
                                                         600/508
(Continued)

OTHER PUBLICATIONS

Boccanfuso et al., "Remote Measurement of Breathing Rate in Real Time Using a High Precision, Single-Point Infrared Temperature Sensor," Jun. 24, 2012, Biomedical Robotics and biomechatronics.*
(Continued)

*Primary Examiner* — Baisakhi Roy
*Assistant Examiner* — Jason M Ip
(74) *Attorney, Agent, or Firm* — Morris & Kamlay LLP

(57) ABSTRACT

A device may emit a first emission sequence of infrared radiation at a subject, and capture a first reflected sequence of infrared radiation reflected from the subject. The first emission sequence may be compared to the first reflected sequence, and, based on the comparison, a sequence of variations may be determined. The sequence of variations may be compared to a signal pattern stored in a sleep profile for the subject. The subject may be determined to have exhibited a sleep behavior based on the comparison of the sequence of variations to the signal pattern stored in the sleep profile. In response to determining that the subject has exhibited the sleep behavior, the device may capture a second reflected sequence of radiation reflected from the subject. A breathing rate of the subject and/or a heart rate of the subject may be determined based on the second reflected sequence.

30 Claims, 12 Drawing Sheets

(51) Int. Cl.
*A61B 5/024* (2006.01)
*A61B 5/08* (2006.01)
*A61B 5/0205* (2006.01)

(52) U.S. Cl.
CPC .......... *A61B 5/0816* (2013.01); *A61B 5/4806* (2013.01); *A61B 5/4809* (2013.01); *A61B 5/746* (2013.01)

(56) References Cited

U.S. PATENT DOCUMENTS

| | | | |
|---|---|---|---|
| 6,223,064 B1* | 4/2001 | Lynn | A61B 5/14551 600/324 |
| 6,529,752 B2 | 3/2003 | Krausman et al. | |
| 7,256,899 B1 | 8/2007 | Faul et al. | |
| 7,570,785 B2 | 8/2009 | Breed | |
| 7,659,995 B2 | 2/2010 | Knighton et al. | |
| 7,840,031 B2 | 11/2010 | Albertson et al. | |
| 8,050,461 B2 | 11/2011 | Shpunt et al. | |
| 8,150,142 B2 | 4/2012 | Freedman et al. | |
| 8,249,334 B2 | 8/2012 | Berliner et al. | |
| 8,350,847 B2 | 1/2013 | Shpunt | |
| 8,363,098 B2 | 1/2013 | Rosener et al. | |
| 8,374,397 B2 | 2/2013 | Shpunt et al. | |
| 8,384,997 B2 | 2/2013 | Shpunt et al. | |
| 8,492,696 B2 | 7/2013 | Akerman et al. | |
| 8,493,496 B2 | 7/2013 | Freedman et al. | |
| 8,565,479 B2 | 10/2013 | Gurman et al. | |
| 8,582,867 B2 | 11/2013 | Litvak | |
| 8,594,425 B2 | 11/2013 | Gurman et al. | |
| 8,717,417 B2 | 5/2014 | Sali et al. | |
| 8,749,796 B2 | 6/2014 | Pesach et al. | |
| 8,824,737 B2 | 9/2014 | Gurman et al. | |
| 8,890,809 B2 | 11/2014 | Izumi | |
| 8,934,675 B2 | 1/2015 | Dal Mutto et al. | |
| 8,977,347 B2 | 3/2015 | Madhu et al. | |
| 2006/0241708 A1* | 10/2006 | Boute | A61B 5/0452 607/17 |
| 2009/0183125 A1 | 7/2009 | Magal et al. | |
| 2010/0020078 A1 | 1/2010 | Shpunt | |
| 2010/0152543 A1 | 6/2010 | Heneghan | |
| 2010/0238041 A1 | 9/2010 | Acedo et al. | |
| 2010/0277411 A1 | 11/2010 | Yee et al. | |
| 2011/0268365 A1 | 11/2011 | Lou et al. | |
| 2012/0105326 A1 | 5/2012 | Jeong et al. | |
| 2012/0119988 A1 | 5/2012 | Izumi | |
| 2012/0271199 A1* | 10/2012 | Salisbury | A61B 48/18 600/586 |
| 2013/0014052 A1 | 1/2013 | Frey et al. | |
| 2013/0038881 A1* | 2/2013 | Pesach | G01B 11/25 356/610 |
| 2013/0255154 A1 | 10/2013 | Kanki et al. | |
| 2013/0265227 A1 | 10/2013 | Julian | |
| 2013/0296660 A1 | 11/2013 | Tsien et al. | |
| 2013/0307775 A1 | 11/2013 | Raynor | |
| 2014/0036235 A1 | 2/2014 | Chang et al. | |
| 2014/0046184 A1* | 2/2014 | Heinrich | A61B 5/0064 600/438 |
| 2014/0208274 A1 | 7/2014 | Smyth et al. | |
| 2014/0316293 A1 | 10/2014 | Ahmad et al. | |
| 2014/0334669 A1 | 11/2014 | Acharya | |

OTHER PUBLICATIONS

Kruger et al., "Sleep Detection Using a Depth Camera," 2014, International Conference on Computational Science and Its Applications, vol. 8579, pp. 824-835.*
"Non-contact, automated cardiac pulse measurements using video imaging and blind source separation" by M. Poh et al. Optics Express. vol. 18, No. 10. pp. 10762-10774. May 10, 2010.*
Alhwarin, et al., "IR stereo kinect: improving depth images by combining structured light with IR stereo", InPRICAI 2014: Trends in Artificial Intelligence, pp. 409-421. Springer International Publishing, 2014.
Boccanfuso, et al., "Remote Measurement of Breathing Rate in Real Time Using a High Precision, Single-Point Infrared Temperature Sensor", Department of Computer Science and Engineering University of South Carolina, 6 pages.
Bourlai, "Identifying Humans at Night with Face or Ear Recognition", IDGA (2014).
Gantenbein, "Helping Kinect Recognize Faces", Microsoft Research (2011).
Geng, "Structured-light 3D surface imaging: a tutorial", Advances in Optics and Photonics 3, No. 2 (2011): 128-160.
Henry, et al., "RGB-D mapping: Using depth cameras for dense 3D modeling of indoor environments", In Experimental robotics, pp. 477-491. Springer Berlin Heidelberg, 2014.
Iber, et al., "The AASM manual for the scoring of sleep and associated events: rules, terminology and technical specifications", American Academy of Sleep Medicine, and Conrad Iber. The AASM manual for the scoring of sleep and associated events: rules, terminology and technical specifications. American Academy of Sleep Medicine, 2007., 57 pages.
Li, "Time-of-Flight Camera—An Introduction", Texas Instruments-Technical White Paper (2014).
Nejad, et al., "Comparison of TOF, FMCW and phase-shift laser range-finding methods by simulation and measurement", Quart. J. Technol. Educ 1 (2006): 11-18.
Rashidi, et al., "A survey on ambient-assisted living tools for older adults", Biomedical and Health Informatics, IEEE Journal of 17, No. 3 (2013): 579-590.
Salvi, et al., "A state of the art in structured light patterns for surface profilometry", Pattern recognition 43, No. 8 (2010): 2666-2680.
Scanaill, et al., "A review of approaches to mobility telemonitoring of the elderly in their living environment", Annals of Biomedical Engineering 34, No. 4 (2006): 547-563.
Silberman, et al., "Indoor scene segmentation using a structured light sensor", In Computer Vision Workshops (ICCV Workshops), 2011 IEEE International Conference on, pp. 601-608. IEEE, 2011.
Zhao, et al., "Remote Measurements of Heart and Respiration Rates for Telemedicine", Remote Measurements of Heart and Respiration Rates for Telemedicine. PLoS One 8(10): e71384. doi:10.1371/journal.pone.0071384, pp. 1-14.
Zhu, et al., "Fusion of time-of-flight depth and stereo for high accuracy depth maps", In Computer Vision and Pattern Recognition, 2008. CVPR 2008. IEEE Conference on, pp. 1-8. IEEE, 2008.
Krueger, Bjoern, et al. "Sleep Detection Using a Depth Camera", 14th International Conference, Guimaraes, Portugal, Jun. 30-Jul. 3, 2014, published in Computational Science and Its Applications, ICCSA 2014.†
Bernacchia, Natascia, et al. "Non Contact Measurement of Heart and Respiration Rates based on Kinect", 2014 IEEE International Symposium on Medical Measurements and Applications (MeMeA), Jun. 2014, published in IEEE Xplore, Jul. 24, 2014.†
Lun, Roanna, et al. "A Survey of Applications and Human Motion Recognition with Microsoft Kinect", published in the International Journal of Pattern Recognition and Artificial Intelligence on May 26, 2015.†
Lee, Jaehoon, et al. "Sleep Monitoring System Using Kinect Sensor", published in the International Journal of Distributed Sensor Networks, vol. 2015, Jan. 2015.†
Pereira, Carina Barbosa, et al. "Remote Monitoring of Breathing Dynamics Using Infrared Thermography", 2015, 37th Annual International Conference of the IEEE Engineering in Medicine and Biology Society (EMBC), Aug. 25-29, 2015, accepted and published on Sep. 14, 2014 by Optical Society of America.†
Falie, D., et al. "Sleep Monitoring and Sleep Apnea Event Detection Using a 3D Camera", published in the International Conference on Communications (COMM),Jun. 10-12, 2010, further published in IEEE Xplore Jul. 15, 2010, IEEE.†
NHLBI: Health Information for the Public, U.S. Department of Health and Human Services, Jul. 10, 2012. Https://www.nhlbi.nih.gov/health/health-topics/topics/sleepapnea/.†

\* cited by examiner
† cited by third party

USING ACTIVE IR SENSOR TO MONITOR SLEEP

BACKGROUND

Conventional sleep monitoring systems that measure physiological parameters, such as a person's heart rate or breathing rate, require sensors to be in contact with the person. Contact sensors are often uncomfortable for people to wear for long periods of time. The disadvantages of contact sensors are magnified during sleep studies, where the presence of the sensors can influence a person's sleep patterns. Similarly, when monitoring the sleep of an infant, contact sensors often interfere with infant's ability to sleep and otherwise inhibit the infant's interaction with the world around them.

In addition, events detected by sleep monitoring systems, such as dangerously low breathing rates, often require an emergency response. Many homes rely on home automation systems to trigger emergency responses; however, conventional sleep monitoring systems do not interface with broader home automation systems. Thus, home occupants wishing to receive health alerts via their home automation system cannot do so.

BRIEF SUMMARY

According to an implementation of the disclosed subject matter, a device may emit a first emission sequence of radiation at a subject, and a device may capture a first reflected sequence of radiation reflected from the subject. The first emission sequence may be compared to the first reflected sequence, and, based on the comparison of the first emission sequence to the first reflected sequence, a sequence of variations may be determined. The sequence of variations may be compared to a sleep profile of the subject. The subject may be determined to have exhibited sleep behavior based on the comparison of the sequence of variations to the sleep profile. In response to determining the subject has exhibited sleep behavior, a device may capture a second reflected sequence of radiation reflected from the subject. A breathing rate of the subject and/or a heart rate of the subject may be determined based on the second reflected sequence.

According to an implementation of the disclosed subject matter, a device may include a radiation emission component and a radiation capture component. A processor may be in communication with the device, and the processor may be configured to execute instructions. The instructions may include emitting from a radiation emission component, a first emission sequence of radiation at a subject; capturing at a radiation capture component, a first reflected sequence of radiation reflected from the subject; and comparing the first emission sequence to the first reflected sequence. The instructions may include determining a sequence of variations based on the comparison of the first emission sequence to the first reflected sequence; comparing the sequence of variations to a sleep profile of the subject; and determining, based on the comparison of the sequence of variations to the sleep profile, that the subject has exhibited sleep behavior. The instructions may include capturing a second reflected sequence of radiation in response to determining the subject has sleep behavior and determining, based on the second reflected sequence, a breathing rate of the subject and/or a heart rate of the subject.

According to an implementation of the disclosed subject matter, a non-transitory computer readable medium may store instructions including emitting a first emission sequence of radiation at a subject, capturing a first reflected sequence of radiation reflected from the subject, and comparing the first emission sequence to the first reflected sequence. The instructions may include determining a sequence of variations based on the comparison of the first emission sequence to the first reflected sequence; comparing the sequence of variations to a sleep profile of the subject; and determining, based on the comparison of the sequence of variations to the sleep profile, that the subject has exhibited sleep behavior. The instructions may include capturing a second reflected sequence of radiation in response to determining the subject has exhibited sleep behavior and determining, based on the second reflected sequence, a breathing rate of the subject and/or a heart rate of the subject. The instructions may include comparing the breathing rate and/or the heart rate to a sleep profile of the subject; determining a sleep disorder status based on the comparison of the breathing rate and/or the heart rate to the sleep profile; and providing an alert, based on the sleep disorder status, to a device associated with a user.

According to an implementation of the disclosed subject matter, a means may emit a first emission sequence of radiation at a subject, capture a first reflected sequence of radiation reflected from the subject, and compare the first emission sequence to the first reflected sequence. A means may determine a sequence of variations based on the comparison of the first emission sequence to the first reflected sequence; compare the sequence of variations to a sleep profile of the subject; and determine, based on the comparison of the sequence of variations to the sleep profile, that the subject has exhibited a sleep behavior. A means may capture a second reflected sequence of radiation in response to determining the subject has exhibited sleep behavior and determine, based on the second reflected sequence, a breathing rate of the subject and/or a heart rate of the subject.

Additional features, advantages, and embodiments of the disclosed subject matter may be apparent from consideration of the following detailed description, drawings, and claims. Moreover, it is to be understood that both the foregoing summary and the following detailed description are illustrative and are intended to provide further explanation without limiting the scope of the claims.

BRIEF DESCRIPTION OF THE DRAWINGS

The accompanying drawings, which are included to provide further understanding of the disclosed subject matter, are incorporated in and constitute a part of this specification. The drawings also illustrate embodiments of the disclosed subject matter, and together with the detailed description serve to explain the principles of embodiments of the disclosed subject matter. No attempt is made to show structural details in more detail than may be necessary for a fundamental understanding of the disclosed subject matter and various ways in which it may be practiced.

DETAILED DESCRIPTION

Figure 1A:
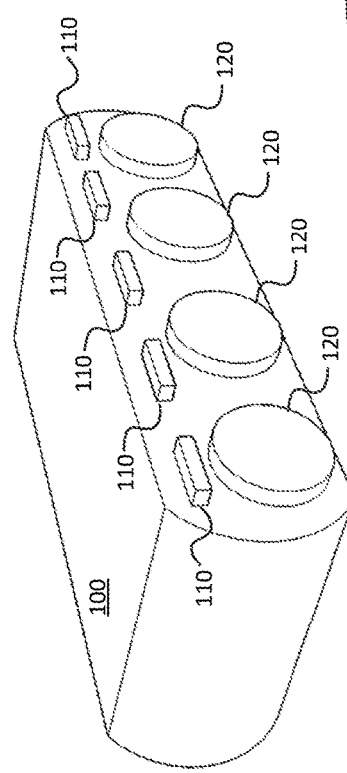
FIG. 1A shows a device that includes radiation emission components and radiation capture components according to an implementation of the disclosed subject matter.

To address the issues previously described, devices, systems, and techniques as disclosed herein may provide for monitoring the sleep of a person using various measured sequences of radiation. For example, a device that emits and captures infrared (IR) light may be located in a person's bedroom within a premises, such as a home. Infrared or near-infrared light will not typically wake or disturb the person because humans do not perceive light having infrared wavelengths. In general, implementations disclosed herein may emit a pattern or sequence of such IR light or, more generally, radiation. By comparing light reflected from a sleeping person to known patterns and sequences, it may be possible to determine a status of the sleeping person, a sleep behavior or disorder, a stage of sleep, or the like, without requiring the sleeping person to wear or maintain a device in contact with her or her person.

In an example implementation, a device may be positioned in the bedroom in a location that enables the device to emit a first emission sequence of radiation into a space in the bedroom that includes the bed. The first emission sequence may be emitted in the pattern of an array from a single emission component or from multiple emission components. The device may capture a first reflected sequence of radiation that is reflected from the space, while a subject lays down to sleep in the bed. The first emission sequence may be compared to the first reflected sequence, and variations between the two sequences may be determined as a sequence of variations. The sequence of variations may correspond to the sequence of elements of the array inhabited by the subject as the subject lays down to sleep. The sequence of variations may be compared to a predetermined sequence of variations that is stored in a sleep profile for the subject. Based on this comparison, it may be determined that the subject has exhibited sleep behavior, where the sleep behavior is behavior indicative that the subject has laid down to sleep.

After determining the subject has exhibited sleep behavior, the device may emit a second emission sequence of infrared radiation directed at the subject and capture a second reflected sequence of infrared radiation reflected from the subject. The second emission sequence may be emitted from a single emission component and may reflect from the subject's skin, clothing, or bedding while the subject is sleeping. The second reflected sequence may be analyzed using signal processing techniques to determine dominant frequencies. Energy peaks may be determined in the dominant frequencies of the second reflected sequence, and these peaks may correspond to breath cycles of the subject. Based on this determination, the breathing rate for the subject may be determined. Aspects of the second reflected sequence may determine to have been reflected from the face of the subject, and these aspects may be analyzed to detect periodic changes in wavelength. These periodic changes in wavelength may correspond to changes in the skin tone of the subject that are caused by variation in blood flow. The heart rate of the subject may be determined based on the rate energy peaks in these wavelengths are detected.

The breathing rate data and heart rate data may be recorded and periodically compared to sleep disorder data. The sleep disorder data may include breathing rate values or heart rate values that correspond to sleep disorders, such as sleep apnea or dangerously low respiration. Sleep disorder data may be stored in the sleep profile for the subject. When the breathing rate or heart rate corresponds to a sleep disorder rate within a threshold amount, a sleep disorder status may be determined and a notice may be provided to a home automation system. This notice may trigger an alert within the home automation system such as sending a message to another occupant of the home or sounding an alarm. For example, if an infant's breathing rate falls to a dangerous level, an alarm may be triggered in a parent's bedroom.

Implementations of the disclosed subject matter may be partially or completely incorporated within home automation systems such as the "smart home environment" described in later portions of this disclosure.

Figure 1B:
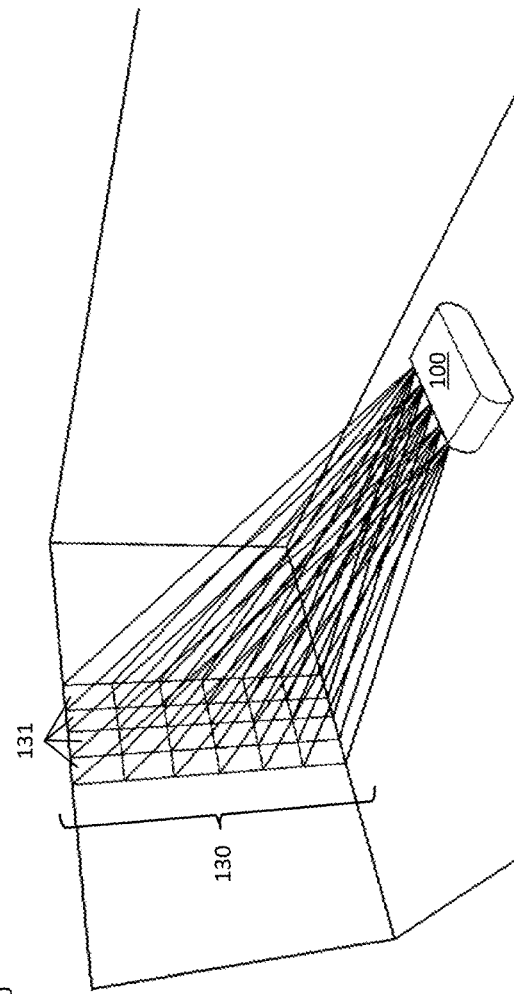
FIG. 1B shows a device emitting radiation according to an implementation of the disclosed subject matter.
Figure 1C:
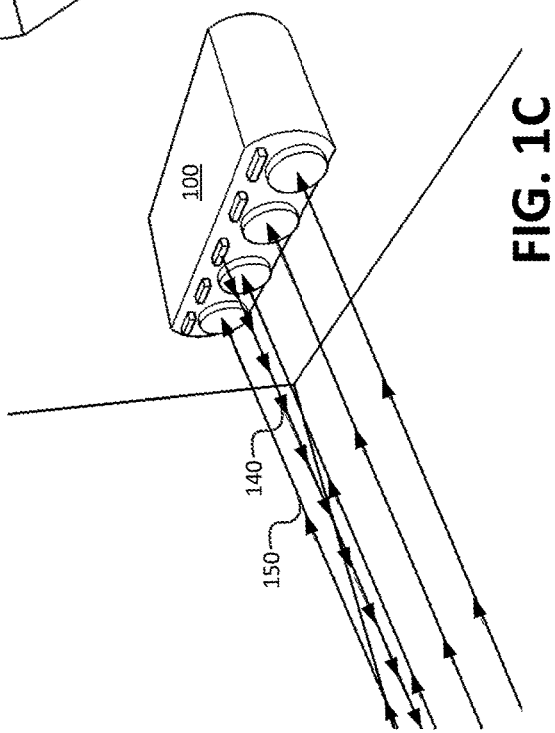
FIG. 1C shows a device emitting and capturing radiation according to an implementation of the disclosed subject matter.

A device for sleep monitoring may include radiation emission components and radiation capture components. The device may also include electronics for operation and control of the device as well as interfacing with other components of a home automation system. For example, FIGS. 1A-1C show a device 100 for radiation emission and radiation capture according to an implementation of the disclosed subject matter. The device may be a stand-alone device, may be incorporated into another device such as bedroom furniture, or coupled to a network in communication with a home automation system, sensor, or other device, such as a home monitoring hub. Any suitable electromagnetic radiation may be emitted from the device, including visible white light, near-infrared radiation, or infrared radiation. The device may emit radiation from emission components 110. The implementation depicted shows five emission components; however the device may include a single emission component or any number of emission components suitable for the purposes of this disclosure. The emission and capture components may be disposed within a single housing or device, as shown, or the emission and capture components may be separate physical devices that are configured to operate in tandem and/or in conjunction with another system such as a smart home system.

In FIG. 1B the emission components are depicted as infrared light emitting diodes (LEDs), however the type of emission component may be any type of component that emits electromagnetic radiation in a manner suitable for the purposes of this disclosure. For example the emission component may be an LED point source, a laser, or a lens-focused light source such as an incandescent lamp or an organic LED. In certain embodiments non-point sources may also be employed. Radiation may be emitted in a pattern 130 such as a certain arrangement of projected pixels, an arrangement of stripes, an array that defines a set of elements 131, and other structured formats or unstructured radiation formats. For purposes of this disclosure, a pattern may include no more than a single element or a pattern may include multiple elements.

The device may capture radiation through capture components 120. Capture components may be any suitable radiation sensor. For example the capture components may be image sensors such as photodiodes, charge-coupled devices (CCD), complementary metal-oxide-semiconductor (CMOS) devices, red green blue (RGB) imaging cameras, RGB-Depth (RGB-D) imaging cameras, infrared imaging sensors, and other components configured to detect electromagnetic radiation. FIG. 1C shows the device emitting radiation 140 from a single emission component and capturing reflected radiation 150 in each image capture component. However radiation may be emitted from some or all emission components and captured by some or all capture components. The implementation depicted shows four capture components; however the device may include a single capture component or any number of capture components suitable for the purposes of this disclosure.

The device may include additional components sufficient to operate and control the radiation emission and capture components and communicate with other components of a home automation system, such as the components of a smart home environment described below. For example, the device may include memory, processors, electronic circuitry, and wireless communication components such as those described with respect to FIGS. 10A-10B, FIG. 11, and FIG. 12 below.

Figure 2:
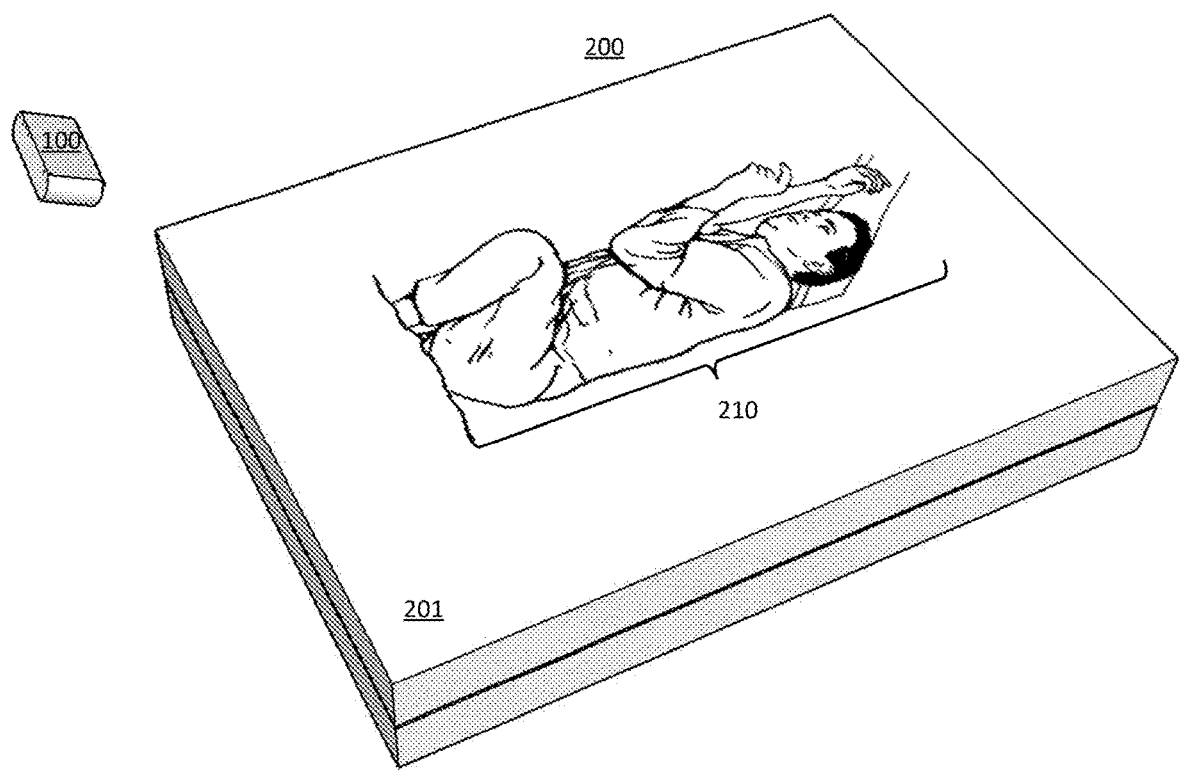
FIG. 2 shows a device for emitting and capturing radiation and a subject according to an implementation of the disclosed subject matter.

In some implementations, the device may be positioned in a room such that it may emit radiation towards a space in the room where a subject sleeps. For example, FIG. 2 shows a room 200, according to an implementation of this disclosure, where the device 100 is positioned over the bed 201. From this position, subject 210, such as a man, may be monitored. The device may be implemented in a range of other objects within the room. For example, the device may be attached to or integrated within furniture such as a bed, night stand, or dresser; a lamp; overhead fan; baby's crib; a mobile over the baby's crib; a lighting fixture; a ceiling, pillar, wall surface or molding; a television, a video monitor, an audio device or other audiovisual equipment; or any other object suitable for the purposes of this disclosure.

The device described above may be implemented as part of a method for monitoring the sleep of a subject. For example, FIG. 3. shows a method 300 for sleep monitoring according to an implementation of the disclosed subject matter. A first sequence of radiation may be emitted at the subject at 310. For example, the device may emit a first emission sequence of infrared radiation from a plurality of emitting components towards a space containing the subject. The sequence of radiation may be emitted in a pattern that defines an array of elements. At 320, a first reflected sequence of radiation reflected from the subject may be captured. For example, the device may capture the first reflected second sequence of infrared radiation at a plurality of radiation capture components housed in the device.

The first emission sequence may be compared to the first reflected sequence at 330, and at 340 a sequence of variations between the first emission sequence and the first reflected sequence may be determined. For example the device may emit a sequence of infrared radiation that define rectangles, which may make up the elements of an array, such as elements 131 shown in FIG. 1B. When a subject goes to sleep, he may walk into a field of view of the device, bend over, lay down on the bed, and roll periodically on the bed. The subject's movements may become more and more infrequent until he falls asleep. This course of movements may reflect the emitted radiation as he passes through different elements of the array. A capture component of the device may capture the radiation reflected by the subject as he moves into a first element and detect the subject based on a variation between the emitted pattern of radiation and captured pattern of radiation. For example, in the absence of reflection from the subject, a line of radiation of the emitted sequence of radiation may be anticipated to be in a predetermined location; however when the line of radiation reflects from the subject in its path, the location may vary from this predetermined location. Based on this variation, the presence of the subject may be detected crossing into or out of an element of the array. This process may repeat as the subject moves through various elements in the array in the course of walking into the field of view of the array, bending over, laying down on the bed, and rolling around on the bed, and falling asleep. Each of these variations in the emitted and reflected radiation may be combined to make up a sequence of variations. This sequence of variations, including the time between when variations are detected, may be characteristic of the subject's behavior when he goes to bed. Thus the sequence of variations may define a sleep behavior. Detecting this sleep behavior may be used to distinguish between times in which the subject has merely gone to bed, and those in which other events take place within the field of view of the device, such as when the subject is watching television or when a pet jumps onto the bed.

Depth within the array may also be determined, resulting in a variation that represents a three dimensional location of the subject. For example, a depth of the subject may be determined through modulated time of flight sensing techniques that detect a variation in a the phase of a carrier signal between the first emission sequence of radiation and the first reflected sequence of radiation. In this way the distance between the device and the subject from whom the radiation is reflected may be determined and combined into a three dimensional location of the subject. Each successive three dimensional location may be combined as above to make up a sequence of variations corresponding to three dimensional locations of the subject.

Various techniques, such as structured light techniques, stereo techniques, and time-of-flight sensing, may be employed when determining the location of the subject. For example, fixed or programmable structured light techniques may be employed to detect variations in a pattern of radiation, such as the dimensional spreading, geometrical skewing, or depth of the pattern's elements, in order to determine information about an object. An example of such a technique is provided in Geng, Jason, "Structured-light 3D surface imaging: a tutorial", *Advances in Optics and Photonics* 3, no. 2 (2011): 128-160. In addition, stereo techniques may be employed to detect a variation between the location of an aspect of a pattern of radiation captured in a first capture component and the location of the aspect in a second capture component. This variation may be used to determine location and depth information of the object from which the pattern is reflected. An example of such a technique is provided in Alhwarin, Faraj, et al., "IR stereo kinect: improving depth images by combining structured light with IR stereo", *PRICAI* 2014: *Trends in Artificial Intelligence*, pp. 409-421, Springer International Publishing, 2014. As another example, a time-of-flight variation may be measured between a pulse emission of a pattern of radiation and the captured reflection of that pattern of radiation, or a time-of-flight variation may be measured by determining the phase shift between an emitted pattern of radiation modulated by a continuous wave and the captured reflection of that pattern of radiation. Time-of-flight variations such as these may be used to determine location and depth information of an object. An example of such a technique is provided in Zhu, Jiejie et al., "Fusion of time-of-flight depth and stereo for high accuracy depth maps", *Computer Vision and Pattern Recognition,* 2008, CVPR 2008. IEEE Conference on, pp. 1-8, IEEE, 2008.

Figure 3:
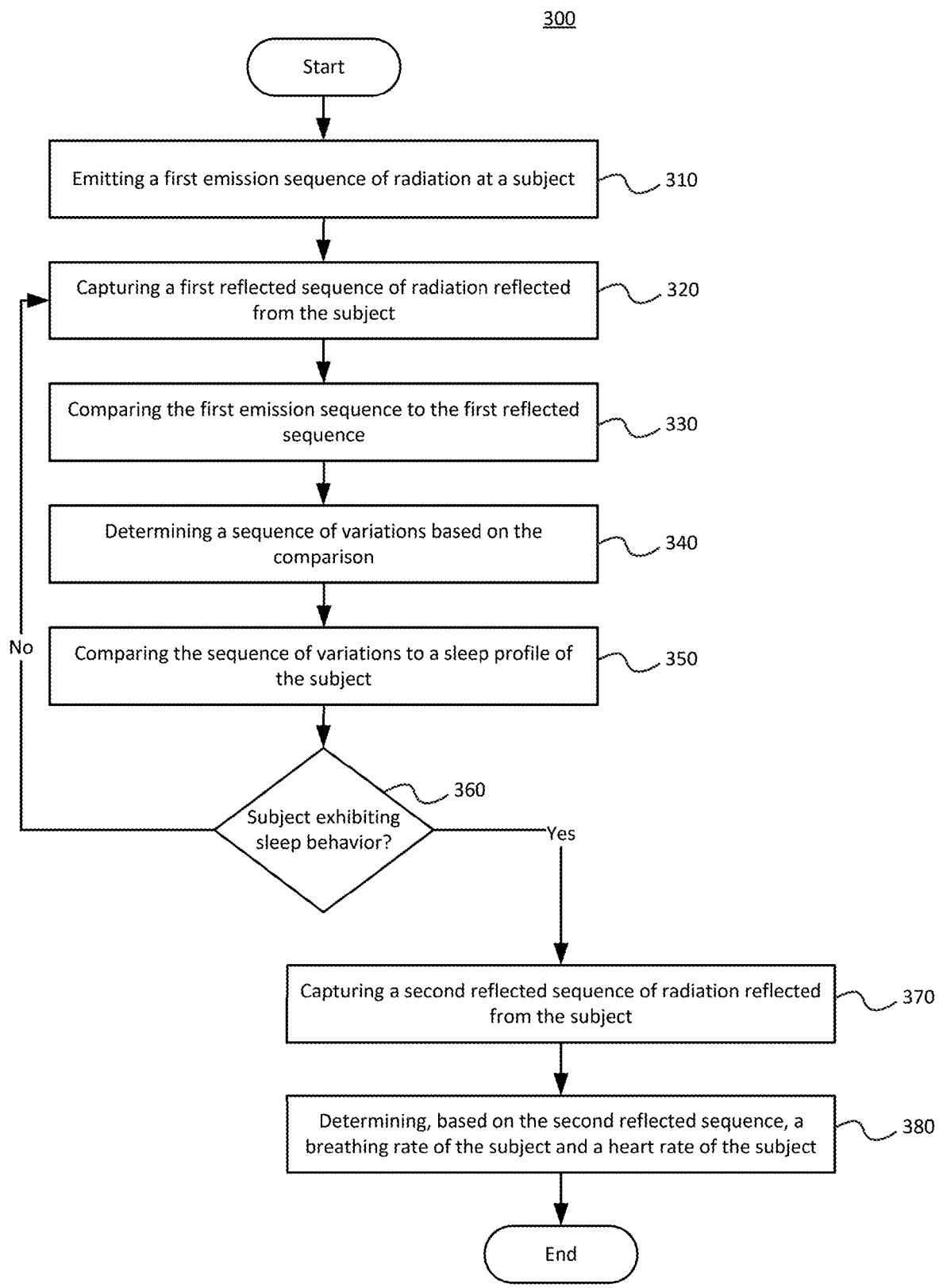
FIG. 3 shows a method for monitoring sleep according to an implementation of the disclosed subject matter.

Continuing the description of FIG. 3, the sequence of variations may be compared to a sleep profile of the subject at 350, and based on this comparison, it may be determined that the subject is exhibiting sleep behavior at 360. For example, a sequence of variations corresponding to the subject going to bed may be stored in a sleep profile of the subject. The determined sequence of variations may be compared to the stored sequence of variations and the discrepancy may be measured. For example, the stored sequence of variations may correspond to a sequence of coordinates of the subject has moved through in the past when he goes to sleep. The determined sequence of variations may correspond to a sequence of coordinates of the subject as he is going to sleep in the present. The sequences may be compared and the discrepancies between the each set of coordinates quantified. This quantity may be compared to a threshold value. If the quantity is below the threshold then it may be determined the subject has laid down to go to sleep.

The threshold for detecting sleep behavior may be determined empirically. For example the device may collect data from the subject as the subject goes to sleep over a period of time and determine an average statistical variance in the determined sequences of variations. This variance may serve as the threshold value. The threshold also may be a configuration of the subject matter of this disclosure. For example a user may specify the threshold value based on the degree of sensitivity desired.

Once a subject has been determined to be exhibiting sleep behavior, the subject may be monitored, and a breathing rate or heart rate of the subject may be determined. For example, at 370 a second reflected sequence of radiation reflected from the subject may be captured. The second reflected sequence may be reflected from radiation that originated as some or all of the first emission sequence, or the second reflected sequence may be reflected from a distinct sequence of radiation emitted from the device. At 380 based on the second reflected sequence, a breathing rate of the subject and a heart rate of the subject may be determined. The second reflected sequence may be radiation reflected from a single component, such as an LED point source, or it may be radiation reflected from multiple components.

The breathing rate of the subject may be determined according to various techniques. For example, body surface movements in the chest and abdomen area due to respiration may alter the distance between the subject and the device capturing reflected radiation, as well as the geometry of the reflecting surfaces of the subject. For example, the subject may inhale and the subject's chest may expand. This expansion may shorten the distance between the radiation capture component and the subject, or the expansion may alter the angle of bedding surface covering the subject's chest and thus increase or decrease the surface area reflecting radiation. Movements such as this may increase or decrease parameters of the reflected radiation such as frequency, wavelength, and intensity.

The variations in the second reflected sequence of radiation may be detected and may indicate respiration events. For example, the amount of energy reflected may vary periodically in accordance with the breathing rate due to movements in the subject's chest and abdomen. There may be characteristic peaks or troughs in reflected energy. The breathing rate of the subject may be determined by detecting these variations. Examples of techniques for determining breathing rate may be found in Boccanfuso, Laura, and Jason M. O'Kane. "Remote measurement of breathing rate in real time using a high precision, single-point infrared temperature sensors". *Biomedical Robotics and Biomechatronics (BioRob)*, 2012 *4th IEEE RAS & EMS International Conference on*, pp. 1704-1709 IEEE, 2012. Temperature changes in the skin around the nose and mouth of the subject may also be detected based on reflected infrared radiation and used as a basis for determining breathing rates. Examples of such facial temperature techniques may be found in Zhao, Fang, Meng Li, Yi Qian, and Joe Z. Tsien. "Remote measurements of heart and respiration rates for telemedicine." *PloS one* 8, no. 10 (2013): e71384.

Before determining the breathing rate, the degree of motion of the subject may be determined. In general the deeper the sleep stage of the subject the less movement the subject will exhibit, and thus the less general bodily movement signals may obscure breathing rate signals. Thus, in some implementations, breathing rates may be easier to determine when the subject is in stage 4 sleep than when the subject is in and out of stage 1 sleep. The degree of bodily movement may be determined by analyzing the "noisiness" of the second reflected sequence radiation. If, for example, the second reflected sequence varies more than a threshold amount, then determinations of the breathing rate may be postponed until the subject has entered a deeper sleep stage.

The heart rate of the subject may be determined by detecting variations in the wavelength or related parameters for example: frequency, energy, intensity) of light reflected from the face or other skin surfaces of the subject. For example, a subject's heart rate may be correlated with the rate blood flows through the subject's veins. Changes in blood volume or oxygenation levels in blood may cause changes in skin tone color due to veins beneath the skin. These changes in skin tone may increase the amount of energy in certain wavelengths or frequencies in reflected light. Variations in wavelength or related parameters of the second reflected sequence of radiation may be detected using signal processing techniques. The subject's heart rate may be determined based on the frequency of these parameters. Examples of these techniques may be found in Boccanfuso, Laura, and Jason M. O'Kane mentioned above.

Various techniques may be employed to perform the signal processing tasks discussed herein. For example, statistical techniques, Markov models, state-machine approaches, machine learning techniques, probabilistic models, as well as any other signal processing techniques suitable for the purposes of this disclosure may be employed. Characteristic signal patterns used for determining the phenomena disclosed herein may be made up of distributions of frequencies, wavelengths, energies, intensities, power, or related parameters suitable for the subject matter of this disclosure. Variations may be periodic features within a distribution or between two or more distributions. Variations may be determined by, for example, the signal processing techniques discussed above, as well as other techniques suitable for the purposes of this disclosure.

Figure 4A:
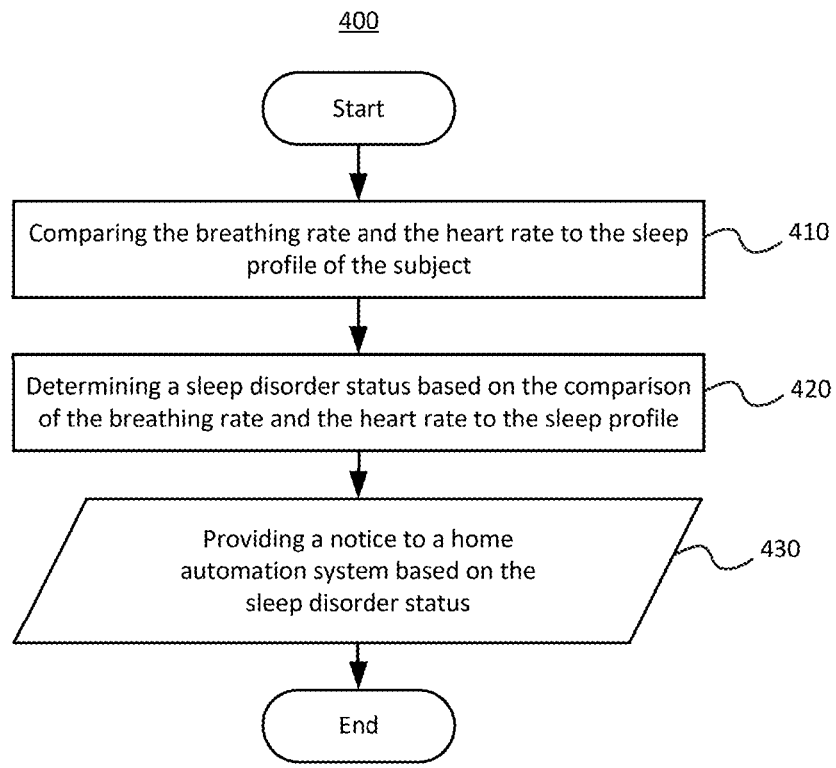
FIG. 4A shows a method for determining a sleep disorder status according to an implementation of the disclosed subject matter.

Sleep disorders may be detected based on the determined breathing rate and heart rate, as well as other signal data. For example, FIG. 4A depicts a method 400 for determining a sleep disorder status according to an implementation of the disclosed subject matter. At 410 the breathing rate and heart rate of the subject may be compared to disorder rates stored in the sleep profile for the subject, and at 420 a sleep disorder status may be determined based on the comparison. A sleep disorder status may be any status of a device or system that is indicative of a sleep disorder exhibited by the subject. For example, a sleep disorder status may be data occupying a field corresponding to a sleep disorder in an application executing on a device or system. A sleep disorder status may include various types of indicators. For example, the sleep disorder status may indicate the particular sleep disorder detected or merely the logical existence of a sleep disorder.

A sleep disorder may be an abnormal heart rate, an abnormal breathing rate, or abnormal movements of the subject as compared to baseline rates and tolerances in a subject's sleep profile. A sleep disorder may also include higher level diagnoses. For example, if a subject is exhibiting a slow and irregular breathing rate, a sleep disorder may be sleep apnea. Subject-specific sleep disorders may be specified within the subject's sleep profile. For example, a sleep disorder may be specified as exhibiting a heart rate within an otherwise generally healthy range if the subject is also known to have a heart condition that renders experiencing such heart rates dangerous. As another example, a sleep disorder may be specified that corresponds to an awake child based on the child moving around when the child should be sleeping. In general a sleep disorder may be any combination of physiological parameters and movements specified as a sleep disorder within a subject's sleep profile.

Figure 4B:
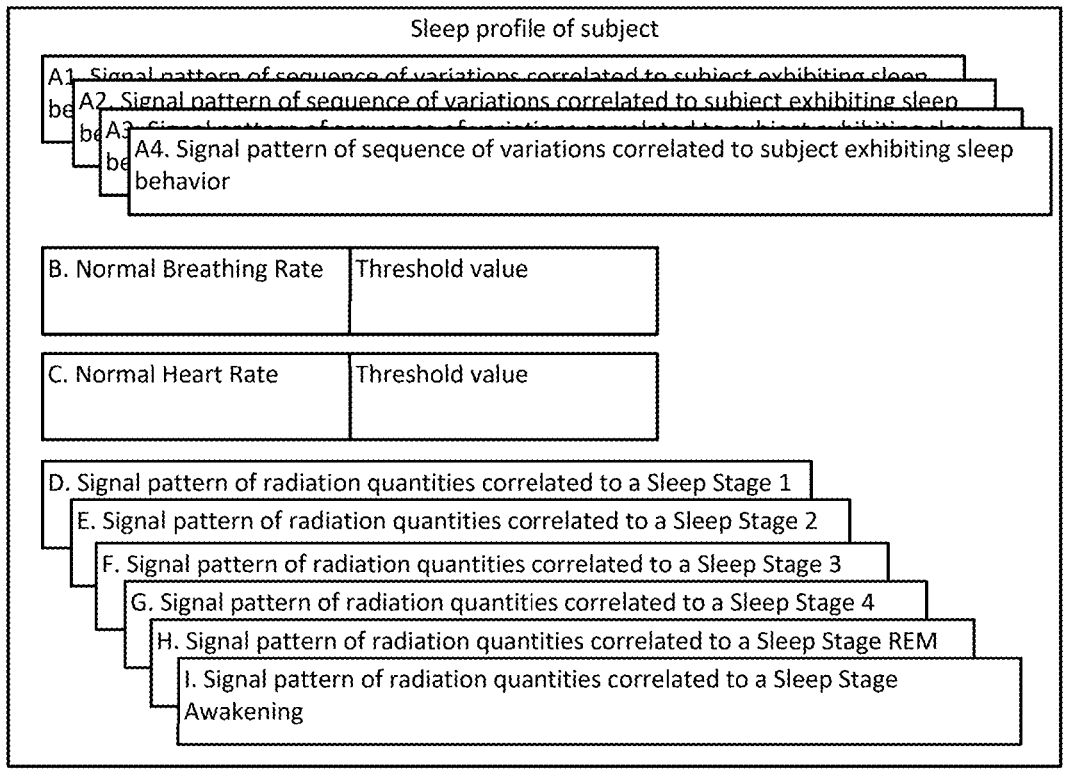
FIG. 4B shows a sleep profile of a subject according to an implementation of the disclosed subject matter.

An example of a sleep profile according to an implementation of the disclosure is shown in FIG. 4B. As show, the profile may store signal patterns A1-A4 made up of a sequence of variations corresponding to the subject exhibiting sleep behavior. These signal patterns may be developed empirically, for example by capturing reflected radiation over a series of events when the subject goes to bed. The multiple variants A1-A4 may correspond to different sleep behaviors exhibited. For example, the subject may have a signal pattern stored for when the subject goes to bed on the left side of the bed, a signal pattern for when the subject goes bed on the right side of the bed, a signal pattern for when the subject's spouse goes to bed with the subject, a signal pattern for when the subject reads a book before going to sleep, a signal pattern for when the subject watches television and then goes to sleep, and so forth. A set of variants may be desirable so that behaviors leading up to the subject exhibiting sleep behavior do not obscure legitimate opportunities to monitor physiological parameters.

The sleep profile may also include, for example, values of the normal breathing rate B for the subject and normal heart rate C for the subject, These may be determined empirically through a series of observations of the subject with the device, or they may be know through other diagnostic methods or received as input from a user. Accompanying the normal breathing rate and normal heart rate data may be threshold values or tolerances. These values may be quantities or ranges that correspond, for example, to empirically determined average variances in the heart rate and breathing rate for the subject; they may be percentages, or they may be configuration values specified for the subject based upon the subject's circumstances. There may also be variants of normal breathing rate B and heart rate C. For example, the subject may exhibit a certain breathing rate within the first hour after the subject goes to bed, but this breathing rate may slow significantly later in the sleep cycle as the subject experiences deeper sleep stages.

The sleep profile may also include additional signal patterns, quantities, ranges, tolerances, and threshold values specified for the subject. For example, a characteristic signal may be determined that corresponds to the various sleep stages D-I the subject experiences. Thus, based on comparing reflected sequences of radiation to these characteristic sleep stage signal patterns, the particular sleep stage the subject is exhibiting may be determined. This may be desirable for determining whether the subject is completing full, healthy sleep cycles, or whether, for example, the subject is not reaching Rapid Eye Movement (REM) sleep. In another example, a signal may be determined that is characteristic of the subject experiencing sleep apnea. Thus, by comparing reflected sequences of radiation to the characteristic sleep apnea signal pattern, it may be determined that the subject is experiencing the sleep disorder of sleep apnea. Determinations based on signal comparisons may also be combined with determinations based on breathing rate determinations to allow for a more robust diagnosis of sleep apnea. As another example, a signal may be determined that is characteristic of the subject moving around after having already gone to sleep. For example, a characteristic signal may be determined based on sequence of variations captured when a child moves through various elements in an emitted array that is projected towards the child's bed.

Returning to FIG. 4A, at 430 a notice may be provided to a home automation system based on the sleep disorder status. As discussed above, the notice may trigger an alert or provide a data stream to other occupants of the home, such as through a home automation system. Further discussion of the notice aspects of this disclosure is provided below.

In some circumstances, it may be desirable to determine the subject has entered a sleep stage before determining the breathing rate of the subject. For example, as mentioned above, it may be advantageous to determine a subject has entered a sleep stage where the subject will not be expected to exhibit significant bodily motion. For example, the subject may "toss and turn" or otherwise adjust the subject's position while sleeping, or the subject may exhibit involuntary movements such as Restless Legs Syndrome, Periodic Limb Movement Disorder, or forms of Myoclonus that adjust the position of the torso. These movements may alter the radiation reflected from the torso of the subject. These additional alterations may introduce nonperiodic variations that distort or mask a signal of periodic phenomena from which a breathing rate may be determined.

Figure 5:
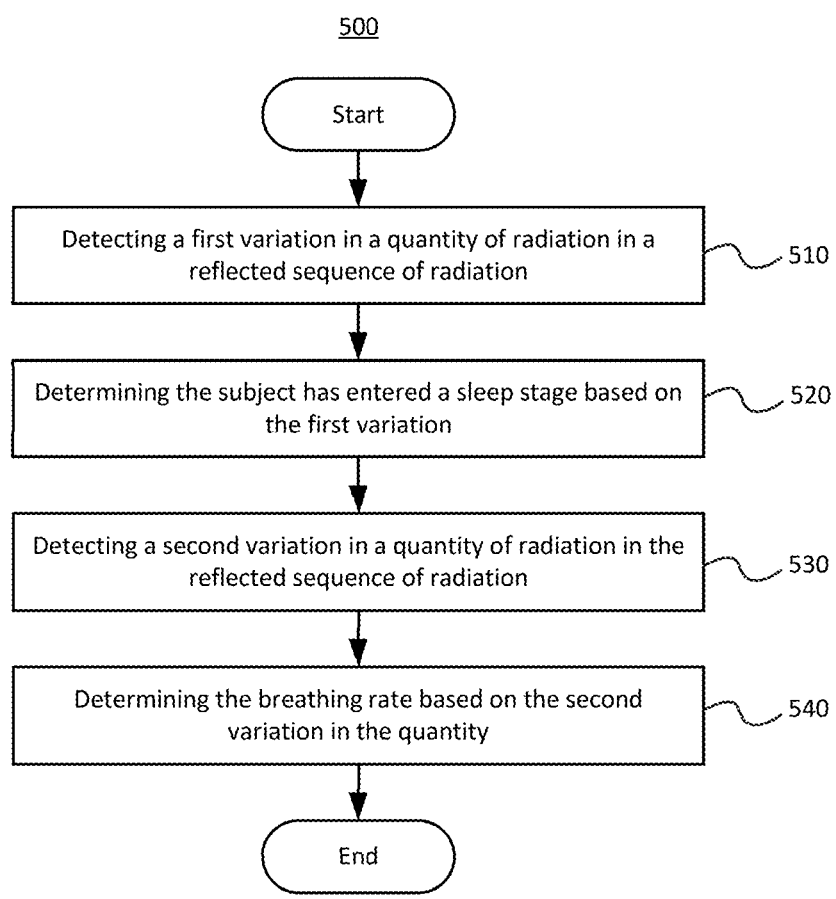
FIG. 5 shows a method for determining a breathing rate of a subject according to an implementation of the disclosed subject matter.

In an example, FIG. 5 depicts a method 500 for determining a breathing rate of a subject according to an implementation of the disclosed subject matter. At 510 a sequence of radiation reflected from the subject is captured and a first variation in a quantity of radiation in the reflected sequence is detected. For example, a signal pattern made up of a series of repeating energy peaks may be detected within the reflected sequence. At 520 the subject may be determined to have entered into a sleep stage. For example the detected signal pattern may be compared to a signal pattern corresponding to a sleep stage stored in the sleep profile for the subject. Based on a degree of similarity between the detected pattern and stored pattern, the subject may be determined to have entered into a particular sleep stage.

A sleep stage may be a recognized sleep stage, such as those set forth in Iber C, Ancoli-Israel S, Chesson A, Quan S F, eds. *The AASM Manual for the Scoring of Sleep and Associated Events: Rules, Terminology, and Technical Specifications,* 1st ed. Westchester, Ill.: American Academy of Sleep Medicine, 2007. For example, a sleep stage may be any of the characteristic periods of time over the course of a subject's sleep cycle, such as the wakefulness stage, stages 1-3, and REM sleep (stage 3 is sometimes recognized as split into stage 3 and stage 4/near-REM sleep). It may be advantageous to determine a subject has entered into a particular recognized sleep stage because the sleep stage may be associated with low bodily movement. For example, by determining that a subject has entered stage 3, it may be determined that the subject is in an advantageous condition for measuring the breathing rate of the subject. Thus by detecting a particular sleep stage, a particular time frame may also be determined when it may be advantageous to determine a breathing rate.

Signal patterns correlated with a sleep stage of a subject may be determined for a subject and stored in the subject's sleep profile for future use. For example, a sleep stage may be detected using methods such as those set forth in the AASM Manual, such as EEG or similar techniques. While these behaviors are being detected, sequences of radiation may be emitted, reflected, and captured by the a radiation capture component of the device disclosed herein. These captured sequences may be analyzed and periodic phenomena may be identified using signal analysis techniques.

For example, periodic phenomena correlated to a specific sleep stage may be identified by detecting dominant energy peaks or related parameters in the signal of the reflected sequence of radiation. These periodic variations may be stored in a sleep profile for the subject. When determining whether the subject has entered a particular sleep stage, sequences of radiation may be captured and compared to these stored signal patterns. Difference between the detected signal pattern and the stored signal pattern may be measured. For example, the difference between a quantity in an energy peak of the captured pattern and the stored pattern may be determined. Other variations may also be detected, such as differences in signal frequency, periods of time when peaks are measured, or the intensity of captured radiation. The sum of differences in energy peak values may be calculated over a period of time and divided by a number of energy peaks to result in an average difference value. This sum may be compared to a threshold value. For example the threshold value may be a standard deviation in energy peak values in the stored signal pattern. Thus for example, if the average difference value is less than the threshold, then the subject may be determined to be in the sleep stage correlated to the stored signal pattern. Other thresholds may also be employed such as the standard deviations of particular populations of subjects, or a threshold may be selected as a configuration for the device. For example, a threshold may be a degree of difference, such as a percentage that the sum of the energy of measured peaks differs from the sum of the energy of the peaks in a stored signal pattern. Other thresholds suitable for the purposes of this disclosure may also be employed.

A sleep stage may also be a selected configuration rather than a particular recognized sleep stage such as those specified in the AASM guidelines. For example, rather than determining a subject is in a particular sleep stage using the techniques described above and then correlating the sleep stage to a signal pattern in reflected radiation, general periodicity in captured radiation may be detected and used as a basis to trigger determination of a breathing rate. This general periodicity may be deemed to be a sleep stage.

For example, a sequence of reflected radiation may be captured and it may be determined that the captured sequence exhibits periodic phenomena within a certain time window. This periodic phenomena may be measured to occur for a period of time, such as 180 seconds. In response to measuring the periodic phenomena for this period of time, it may be determined that it is likely that the periodic phenomena will continue for a sufficient time in the future such that a breathing rate may be measured. For example, characteristic energy peaks in a signal may be determined to occur in a window every 3 to 5 seconds when the subject is sleeping. This signal pattern may be detected for 180 seconds. In response to detecting this signal pattern for 180 seconds, further signal processing may be applied to the sequence of reflected radiation to determine a breathing rate. For example, signal processing techniques may be employed to detect dominant energy peaks within the 3 to 5 second signal window and these dominant peaks may be used as markers for measuring the breathing rate of the subject. In this way, general periodic phenomena may be detected, and the detection of this general periodicity for a period of time may be determined to be a sleep stage of the subject. Detecting the sleep stage of the subject may be used as a trigger from which to determine a breathing rate of the subject.

Thus, as shown in FIG. 5, if the subject has entered into a particular sleep stage, a second variation in a quantity of radiation in the reflected sequence may be detected at 530, and the breathing rate of the subject may be determined at 540, such as in accordance with the techniques discussed above. If the subject is determined at 520 to be in a lower sleep stage, such as stage one, the subject may exhibit more movement than is optimal for determining the breathing rate. Thus, if the sleep stage is not determined to be appropriate, further determinations of the breathing rate be postponed. Whether a particular sleep stage is sufficient for determining a breathing rate may be specific to the subject. Thus conditions optimal for determining breathing rates for a subject may be determined and implemented as a user-specific configuration.

Figure 6:
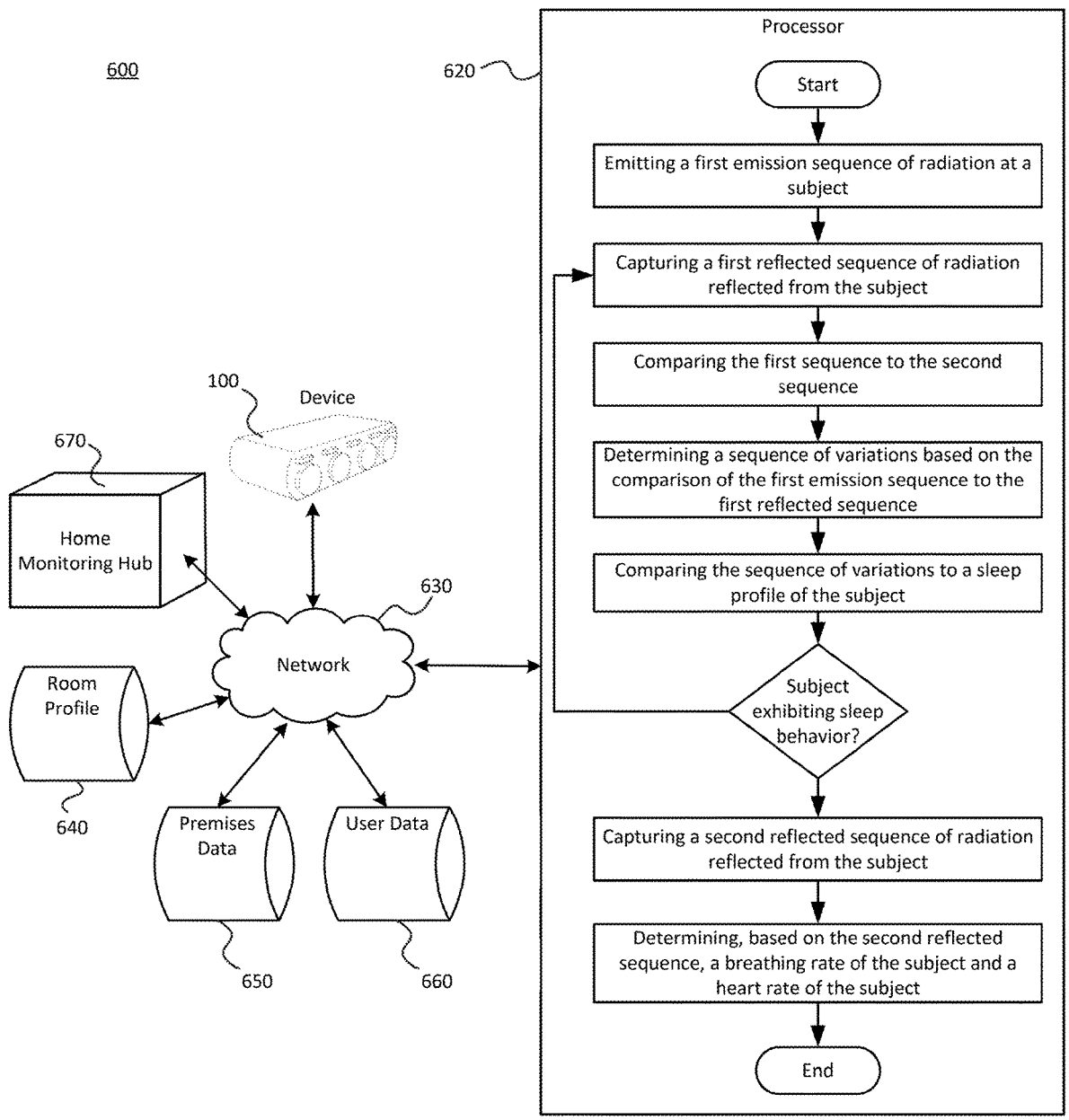
FIG. 6 shows a system for monitoring sleep according to an implementation of the disclosed subject matter.

Implementations of the disclosed subject matter may be embodied in systems such as that disclosed in FIG. 6. System 600 may include device 610 having a radiation emission component and a radiation capture component, and a processor 620 in communication with the device, for example over network 630. The processor may be configured to execute instructions including emitting, from the radiation emission component, a first emission sequence of radiation at a subject and capturing, at the radiation capture component, a first reflected sequence of radiation reflected from the subject. The instructions may include comparing the first emission sequence to the first reflected sequence; determining a sequence of variations based on the comparison of the first emission sequence to the first reflected sequence; comparing the sequence of variations to a sleep profile of the subject; and determining, based on the comparison of the sequence of variations to the sleep profile, that the subject has exhibited sleep behavior. The instructions may further include, in response to determining the subject has exhibited sleep behavior, capturing, at the radiation capture component, a second reflected sequence of radiation and determining, based on the second reflected sequence, a breathing rate of the subject and/or a heart rate of the subject. Instructions, for executing any of the methods or processes disclosed herein, such as those discussed above, may be stored, for example, in a non-transitory computer readable storage medium.

Other components of system 600 may include, for example, room profile 640, premises data 650, and user data 660, all of which may be store in database implemented in storage devices. Home monitoring hub 670 may also be included in the system. These components may be part of a home automation system that may make up or be part of the smart home environment described below. For example, the sleep monitoring techniques described herein may be part of a suit of capabilities integrated into a given room, such as automated lighting systems, automated heating and cooling systems, security systems, and audiovisual systems. Each room may have configurations for these various settings, which may be stored and managed within a room profile for the room. Similarly, each user of a home may have certain user specific configurations for each system of a smart home environment. Configurations for certain subjects may be stored and managed as part of a set of user data for each occupant of the home. Premises data may include data from sensors and data sets associated with the home.

In an example implementation, a sleep monitoring system may receive premises data that indicates the cooling system is malfunctioning. This may result in significantly higher temperatures in a room than those for which the room's sleep profiles were configured. As a result, heart rate determinations may be affected because skin tones may be warmer and thus reflect higher energy signals. The sleep monitoring system may account for this environmental change automatically by filtering certain wavelengths from captured signals or reducing energy peaks by a commensurate amount in order to maintain accurate measurements. The home monitoring hub may coordinate these various system as well as provide management of distributed processing and data storage requirements that support the smart home environment.

Figure 7A:
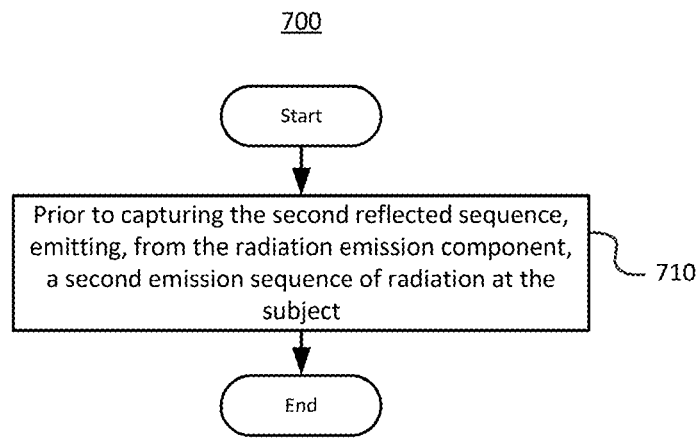
FIG. 7A shows a method for emitting radiation at a subject according to an implementation of the disclosed subject matter.

Implementations disclosed herein may include those in which a single device may emit radiation and capture the radiation. For example, FIG. 7A shows method 700 according to an implementation of the disclosed subject matter, where at 710 the second reflected sequence of radiation captured by the device includes radiation previously emitted from the device and reflected from the subject. This previous emission of radiation may be an emitted sequence of radiation that is distinct from the first emitted sequence of radiation, or it may be part of the first emitted sequence of radiation. In other implementations, one device may emit radiation and another device may capture the radiation, multiple devices may emit radiation and one device may capture the radiation, or one device may emit radiation and multiple devices may capture the radiation. Similarly, each such device may only emit, only capture, or both capture and emit radiation. For example, in some implementations it may be advantageous to have a capturing device in closer proximity to the face of a subject to increase the signal quality gathered from the skin. The emitting device may be positioned further from the subject in order to capture a wider range of sleeping behavior. In general, unless explicitly indicated otherwise herein, any combination of emitting and capturing devices may be used.

Figure 7B:
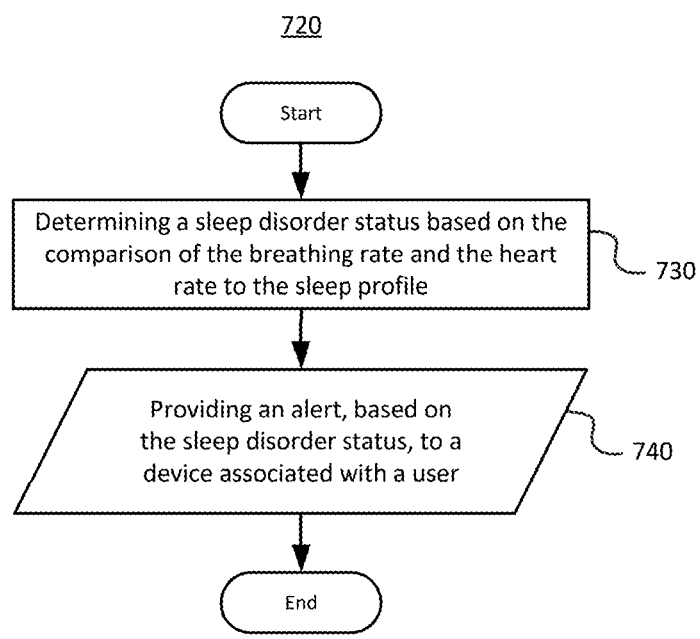
FIG. 7B shows a method for providing an alert to a device associated with a user based on a sleep disorder status according to an implementation of the disclosed subject matter.

Implementations of the disclosed subject matter may provide a notice to a home automation system based on determining a sleep disorder status of a subject. For example, FIG. 7B shows method 720 for providing an alert to a user. At 730 a sleep disorder status for a user may be determined. For example, the subject may be an infant and it may be determined that the subject's breathing rate has fallen below a threshold value. In response to this determination, an alert may be provided to a device associated with a user of the disclosed subject matter at 740. For example, the infant's parent's mobile device may receive an alert. In another example, emergency personnel may be automatically alerted and other components of the smart home environment may be activated. For example, the infant's parent may receive an alert on her mobile device, a home healthcare provider or an emergency responder may be alerted, and a camera in the infant's room may be activated and begin streaming a video feed to the parent's device.

The methods, systems, and devices set forth in the subject matter of this disclosure may be in communication with other methods, systems, and devices throughout a premises. Combined these systems, methods, and devices may make up the greater smart home environment for the premises. Additional aspects of the smart home environment and related components are discussed in the following portions of this disclosure.

In general, a "sensor" as disclosed herein may include multiple sensors or sub-sensors, such as a position sensor that includes both a global positioning sensor (GPS) as well as a wireless network sensor. This combination may provide data that can be correlated with known wireless networks to obtain location information. Multiple sensors may be arranged in a single physical housing, such as where a single device includes movement, temperature, magnetic, and/or other sensors, as well as the devices discussed in earlier portions of this disclosure. Such a housing also may be referred to as a sensor or a sensor device. For clarity, sensors are described with respect to the particular functions they perform and/or the particular physical hardware used, when such specification is necessary for understanding of the embodiments disclosed herein.

Figure 8A:
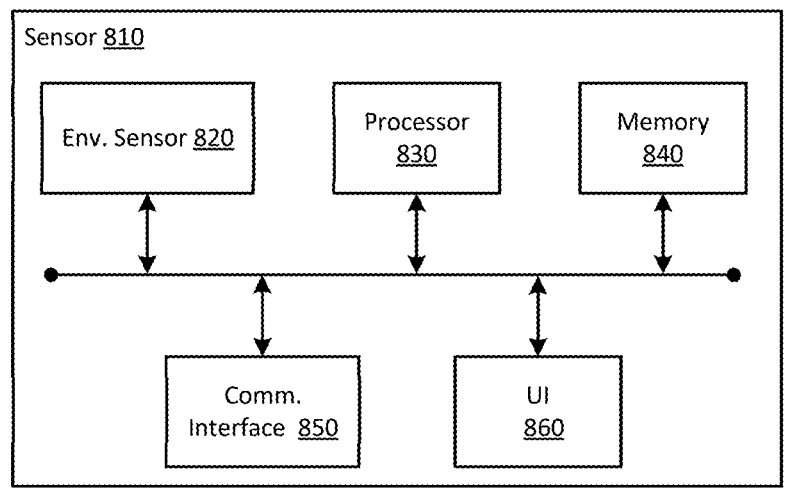
FIG. 8A shows a sensor according to an implementation of the disclosed subject matter.

A sensor may include hardware in addition to the specific physical sensor that obtains information about the environment. FIG. 8A shows an example sensor as disclosed herein. The sensor 810 may include an environmental sensor 820, such as a temperature sensor, smoke sensor, carbon monoxide sensor, motion sensor, accelerometer, proximity sensor, passive infrared (PIR) sensor, magnetic field sensor, radio frequency (RF) sensor, light sensor, such as any of the devices discussed in earlier portions of this disclosure, humidity sensor, pressure sensor, microphone, or any other suitable environmental sensor, that obtains a corresponding type of information about the environment in which the sensor 810 is located. A processor 830 may receive and analyze data obtained by the sensor 810, control operation of other components of the sensor 810, and process communication between the sensor and other devices. The processor 830 may execute instructions stored on a computer-readable memory 840. The memory 840 or another memory in the sensor 810 may also store environmental data obtained by the sensor 810. A communication interface 850, such as a Wi-Fi or other wireless interface, Ethernet or other local network interface, or the like may allow for communication by the sensor 810 with other devices. A user interface (UI) 860 may provide information and/or receive input from a user of the sensor. The UI 860 may include, for example, a speaker to output an audible alarm when an event is detected by the sensor 810. Alternatively, or in addition, the UI 860 may include a light to be activated when an event is detected by the sensor 810. The user interface may be relatively minimal, such as a liquid crystal display (LCD), LED display, or limited-output display, or it may be a full-featured interface such as a touchscreen. Components within the sensor 810 may transmit and receive information to and from one another via an internal bus or other mechanism as will be readily understood by one of skill in the art. One or more components may be implemented in a single physical arrangement, such as where multiple components are implemented on a single integrated circuit. Sensors as disclosed herein may include other components, and/or may not include all of the illustrative components shown.

Figure 8B:
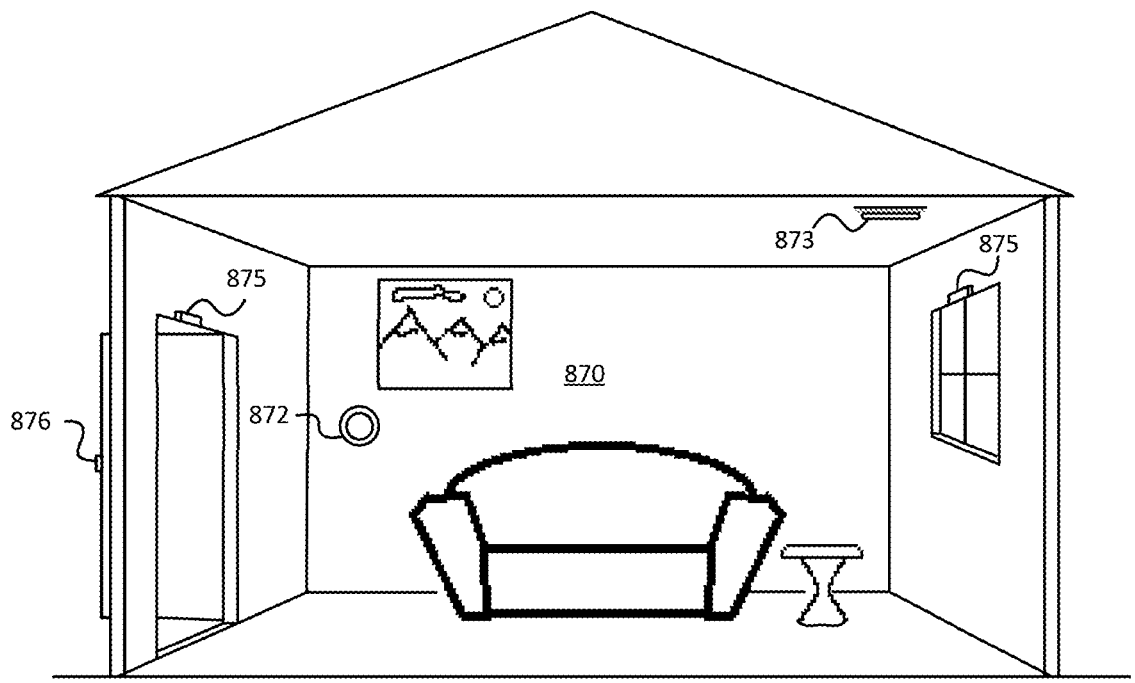
FIG. 8B shows a premises according to an implementation of the disclosed subject matter.

As an example of the implementation of sensors within a premises FIG. 8B depicts, one or more sensors implemented in a home premises 870 as part of a smart home environment. The smart home environment may include multiple types of home automation devices, such as one or more intelligent, multi-sensing, network-connected thermostats 872, one or more intelligent, multi-sensing, network-connected poisonous gas detection units 873, one or more intelligent, multi-sensing, network-connected entry detection units 875, and one or more network-connected door handles 876.

In some configurations, two or more sensors may generate data that can be used by a processor of a system to generate a response and/or infer a state of the environment. For example, an ambient light sensor in a room may determine that the room is dark (e.g., less than 60 lux). A microphone in the room may detect a sound above a set threshold, such as 60 dB. The system processor may determine, based on the data generated by both sensors, that it should activate one or more lights in the room. In the event the processor only received data from the ambient light sensor, the system may not have any basis to alter the state of the lighting in the room. Similarly, if the processor only received data from the microphone, the system may lack sufficient data to determine whether activating the lights in the room is necessary, for example, during the day the room may already be bright or during the night the lights may already be on. As another example, two or more sensors may communicate with one another. Thus, data generated by multiple sensors simultaneously or nearly simultaneously may be used to determine a state of an environment and, based on the determined state, generate a response.

Figure 9A:
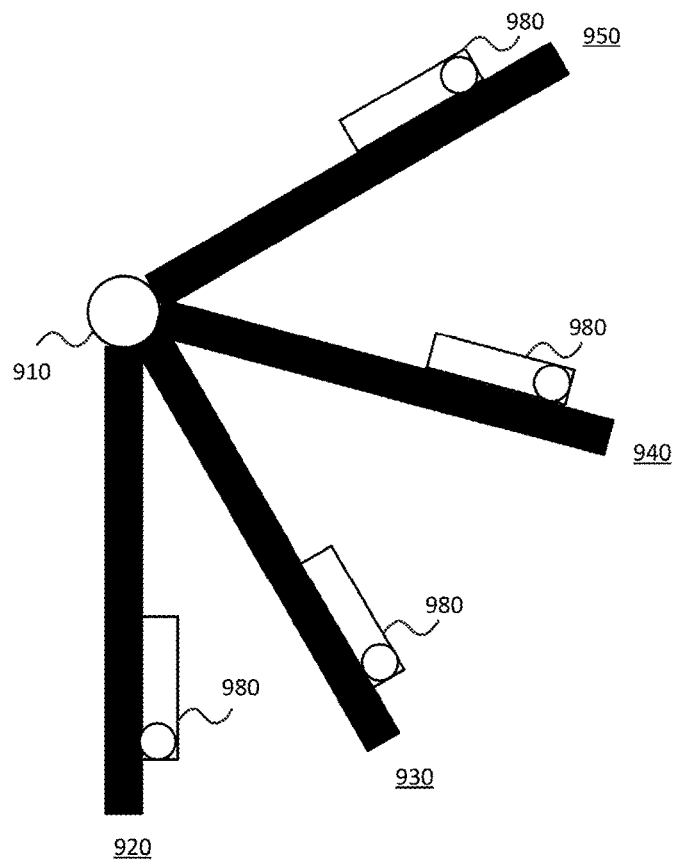
FIG. 9A shows a sensor according to an implementation of the disclosed subject matter.

As another example, a system may employ a magnetometer affixed to a door jamb and a magnet affixed to the door. When the door is closed, the magnetometer may detect the magnetic field emanating from the magnet. If the door is opened, the increased distance may cause the magnetic field near the magnetometer to be too weak to be detected by the magnetometer. If the system is activated, it may interpret such non-detection as the door being ajar or open. In some configurations, a separate sensor or a sensor integrated into one or more of the magnetometer and/or magnet may be incorporated to provide data regarding the status of the door. For example, an accelerometer and/or a compass may be affixed to the door and indicate the status of the door and/or augment the data provided by the magnetometer. FIG. 9A shows a schematic representation of an example of a door that opens by a hinge mechanism 910. In the first position 920, the door is closed and the compass 980 may indicate a first direction. The door may be opened at a variety of positions as shown 930, 940, and 950. The fourth position 950 may represent the maximum amount the door can be opened. Based on the compass 980 readings, the position of the door may be determined and/or distinguished more specifically than merely open or closed. In the second position 930, for example, the door may not be far enough apart for a subject to enter the home. A compass or similar sensor may be used in conjunction with a magnet, such as to more precisely determine a distance from the magnet, or it may be used alone and provide environmental information based on the ambient magnetic field, as with a conventional compass.

Figure 9B:
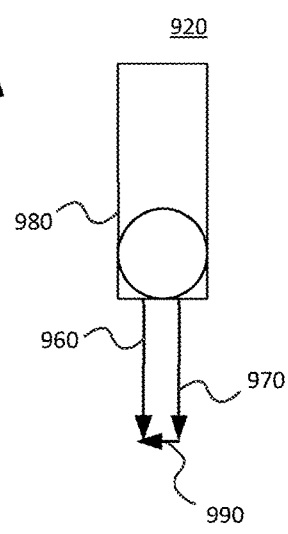
FIG. 9B shows a sensor according to an implementation of the disclosed subject matter.
Figure 9B:
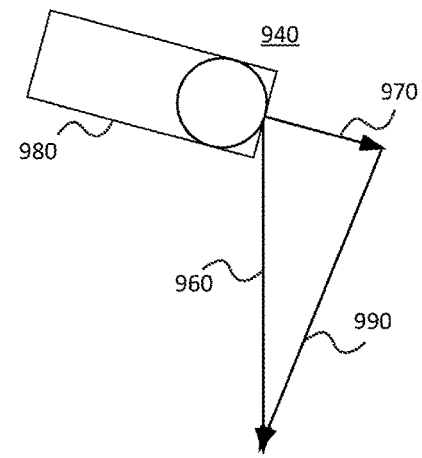

FIG. 9B shows a compass 980 in two different positions, 920 and 940, from FIG. 9A. In the first position 920, the compass detects a first direction 960. The compass's direction is indicated as 970 and it may be a known distance from a particular location. For example, when affixed to a door, the compass may automatically determine the distance from the door jamb or a user may input a distance from the door jamb. The distance 960 representing how far away from the door jamb the door is may be computed by a variety of trigonometric formulas. In the first position 920, the door is indicated as not being separate from the door jamb (i.e., closed). Although features 960 and 970 are shown as distinct in FIG. 9B, they may overlap entirely. In the second position 940, the distance 990 between the door jamb and the door may indicate that the door has been opened wide enough that a subject may enter. Thus, the sensors may be integrated into a home system, mesh network, or work in combination with other sensors positioned in and/or around an environment.

In some configurations, an accelerometer may be employed to indicate how quickly the door is moving. For example, the door may be lightly moving due to a breeze. This may be contrasted with a rapid movement due to a subject swinging the door open. The data generated by the compass, accelerometer, and/or magnetometer may be analyzed and/or provided to a central system such as a controller 1030 and/or remote system 1040 depicted in FIG. 10A. The data may be analyzed to learn a user behavior, an environment state, and/or as a component of a smart home system. While the above example is described in the context of a door, a subject having ordinary skill in the art will appreciate the applicability of the disclosed subject matter to other implementations such as a window, garage door, fireplace doors, vehicle windows/doors, faucet positions (e.g., an outdoor spigot), a gate, seating position, other openings, etc.

The data collected from one or more sensors may be used to determine the physical status and/or occupancy status of a premises. For example, open/close sensors such as door sensors as described with respect to FIGS. 9A and 9B may be used to determine that an unknown subject has entered the premises. The system may first determine that a subject has entered the premises due to sensors detecting a door opening and closing in a time span previously determined to be consistent with a subject entering or leaving the premises. The system next may identify the subject as "unknown" due to the absence of a smartphone, key fob, wearable device, or other device typically used to identify occupants of the premises. Continuing the example, sensor data may be received indicating that a valuable item within the premises has been moved, or that a component of the smart home environment associated with security functions such as a controller disclosed herein, has been moved or damaged. Such sensor data may be received, for example, from a sensor attached to or otherwise associated with the valuable item, from the smart home component itself, or from one or more other sensors within the smart home environment. In response, the system may generate an alert indicating that an unknown subject has entered the premises and/or that the item or component has been moved or damaged. The system may further determine that an occupant of the home is close by but not present in the premises, for example based upon a Wi-Fi signal received from the occupant's smartphone, but an absence of near-field or other short-range communication from the same smartphone. In this case, the system may be configured to send the alert to the occupant's smartphone, such as via SMS, email, or other communication. As another example, the system may determine that the premises is already in an "away" state and that no occupants are nearby or expected to return in the near future. In this case, the system may be configured to send the alert to a local law enforcement agency, such as via email, SMS, recorded phone call, or the like.

Data generated by one or more sensors may indicate patterns in the behavior of one or more users and/or an environment state over time, and thus may be used to "learn" such characteristics. For example, sequences of patterns of radiation may be collected by a capture component of a device in a room of a premises and used as a basis to learn object characteristics of a user, pets, furniture, plants, and other objects in the room. These object characteristics may make up a room profile of the room and may be used to make determinations about objects detected in the room.

In another example, data generated by an ambient light sensor in a room of a house and the time of day may be stored in a local or remote storage medium with the permission of an end user. A processor in communication with the storage medium may compute a behavior based on the data generated by the light sensor. The light sensor data may indicate that the amount of light detected increases until an approximate time or time period, such as 3:30 pm, and then declines until another approximate time or time period, such as 5:30 pm, at which point there is an abrupt increase in the amount of light detected. In many cases, the amount of light detected after the second time period may be either below a dark level of light (e.g., under or equal to 60 lux) or bright (e.g., equal to or above 400 lux). In this example, the data may indicate that after 5:30 pm, an occupant is turning on/off a light as the occupant of the room in which the sensor is located enters/leaves the room. At other times, the light sensor data may indicate that no lights are turned on/off in the room. The system, therefore, may learn occupants' patterns of turning on and off lights, and may generate a response to the learned behavior. For example, at 5:30 pm, a smart home environment or other sensor network may automatically activate the lights in the room if it detects an occupant in proximity to the home. In some embodiments, such behavior patterns may be verified using other sensors. Continuing the example, user behavior regarding specific lights may be verified and/or further refined based upon states of, or data gathered by, smart switches, outlets, lamps, and the like.

Such learning behavior may be implemented in accordance with the techniques disclosed herein. For example, a smart home environment as disclosed herein may be configured to learn appropriate notices to generate or other actions to take in response to a determination that a notice should be generated, and/or appropriate recipients of a particular notice or type of notice. As a specific example, a smart home environment may determine that after a notice has been sent to a first occupant of the smart home premises indicating that a window in a room has been left open, a second occupant is always detected in the room within a threshold time period, and the window is closed shortly thereafter. After making such a determination, in future occurrences the notice may be sent to the second occupant or to both occupants for the purposes of improving the efficacy of the notice. In an embodiment, such "learned" behaviors may be reviewed, overridden, modified, or the like by a user of the system, such as via a computer-provided interface to a smart home environment as disclosed herein.

Sensors as disclosed herein may operate within a communication network, such as a conventional wireless network, and/or a sensor-specific network through which sensors may communicate with one another and/or with dedicated other devices. In some configurations one or more sensors may provide information to one or more other sensors, to a central controller, or to any other device capable of communicating on a network with the one or more sensors. A central controller may be general- or special-purpose. For example, one type of central controller is a home automation network that collects and analyzes data from one or more sensors within the home. Another example of a central controller is a special-purpose controller that is dedicated to a subset of functions, such as a security controller that collects and analyzes sensor data primarily or exclusively as it relates to various security considerations for a location. A central controller may be located locally with respect to the sensors with which it communicates and from which it obtains sensor data, such as in the case where it is positioned within a home that includes a home automation and/or sensor network. Alternatively or in addition, a central controller as disclosed herein may be remote from the sensors, such as where the central controller is implemented as a cloud-based system that communicates with multiple sensors, which may be located at multiple locations and may be local or remote with respect to one another.

Figure 10A:
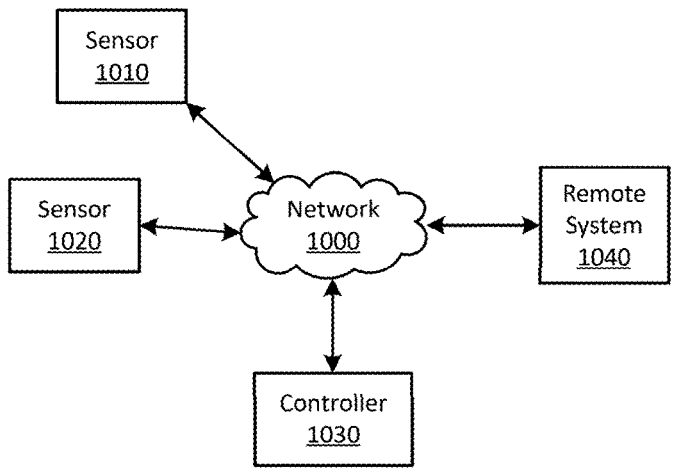
FIG. 10A shows networked sensors according to an implementation of the disclosed subject matter.
Figure 10B:
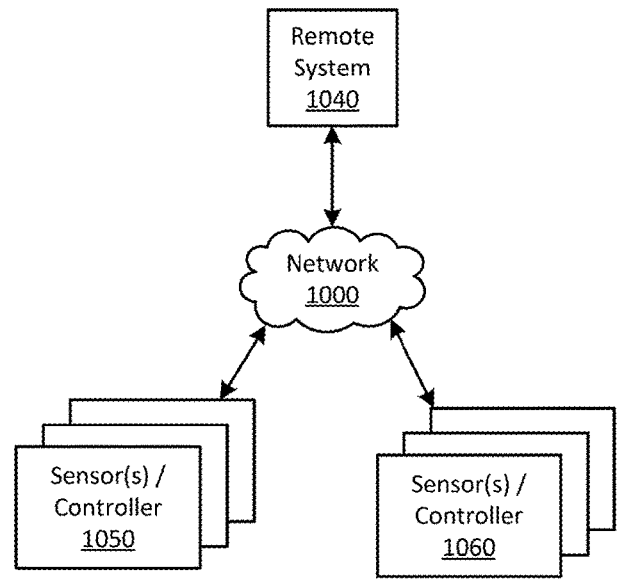
FIG. 10B shows networked sensors according to an implementation of the disclosed subject matter.

FIG. 10A shows an example of a sensor network as disclosed herein, which may be implemented over any suitable wired and/or wireless communication networks. One or more sensors 1010 and 1020 may communicate via a local network 1000, such as a Wi-Fi or other suitable network, with each other and/or with a controller 1030. The controller may be a general- or special-purpose computer. The controller may, for example, receive, aggregate, and/or analyze environmental information received from the sensors 1010 and 1020. The sensors 1010 and 1020 and the controller 1030 may be located locally to one another, such as within a single dwelling, office space, building, room, or the like, or they may be remote from each other, such as where the controller 1030 is implemented in a remote system 1040 such as a cloud-based reporting and/or analysis system. Alternatively or in addition, sensors may communicate directly with a remote system 1040. The remote system 1040 may, for example, aggregate data from multiple locations, provide instruction, software updates, and/or aggregated data to a controller 1030 and/or sensors 1010, 1020.

The devices of the disclosed subject matter may be communicatively connected via the network 1000, which may be a mesh-type network such as Thread, which provides network architecture and/or protocols for devices to communicate with one another. Typical home networks may have a single device point of communications. Such networks may be prone to failure, such that devices of the network cannot communicate with one another when the single device point does not operate normally. The mesh-type network of Thread, which may be used in methods and systems of the disclosed subject matter may avoid communication using a single device. That is, in the mesh-type network, such as network 1000, there is no single point of communication that may fail so as to prohibit devices coupled to the network from communicating with one another.

The communication and network protocols used by the devices communicatively coupled to the network 1000 may provide secure communications, minimize the amount of power used (i.e., be power efficient), and support a wide variety of devices and/or products in a home, such as appliances, access control, climate control, energy management, lighting, safety, and security. For example, the protocols supported by the network and the devices connected thereto may have an open protocol which may carry IPv6 natively.

The Thread network, such as network 1000, may be easy to set up and secure to use. The network 1000 may use an authentication scheme, such as AES (Advanced Encryption Standard) encryption or the like, to reduce and/or minimize security holes that exist in other wireless protocols. The Thread network may be scalable to connect devices (e.g., 2, 5, 10, 20, 50, 100, 150, 200, or more devices) into a single network supporting multiple hops (e.g., so as to provide communications between devices when one or more nodes of the network is not operating normally). The network 1000, which may be a Thread network, may provide security at the network and application layers. One or more devices communicatively coupled to the network 1000 (e.g., controller 1030, remote system 1040, and the like) may store product install codes to ensure only authorized devices can join the network 1000. One or more operations and communications of network 1000 may use cryptography, such as public-key cryptography.

The devices communicatively coupled to the network 1000 of the smart home environment disclosed herein may have low power consumption and/or reduced power consumption. That is, devices efficiently communicate to with one another and operate to provide functionality to the user, where the devices may have reduced battery size and increased battery lifetimes over conventional devices. The devices may include sleep modes to increase battery life and reduce power requirements. For example, communications between devices coupled to the network 1000 may use the power-efficient IEEE 802.15.4 MAC/PHY protocol. In embodiments of the disclosed subject matter, short messaging between devices on the network 1000 may conserve bandwidth and power. The routing protocol of the network 1000 may reduce network overhead and latency. The communication interfaces of the devices coupled to the smart home environment may include wireless system-on-chips to support the low-power, secure, stable, and/or scalable communications network 1000.

The sensor network shown in FIG. 10A may be an example of a smart home environment. The depicted smart home environment may include a structure, a house, office building, garage, mobile home, or the like. The devices of the smart home environment, such as the sensors 1010 and 1020 the controller 1030, and the network 1000 may be integrated into a smart home environment that does not include an entire structure, such as an apartment, condominium, or office space.

The smart home environment can control and/or be coupled to devices outside of the structure. For example, one or more of the sensors 1010 and 1020 may be located outside the structure, for example, at one or more distances from the structure (e.g., sensors 1010 and 1020 may be disposed outside the structure, at points along a land perimeter on which the structure is located, and the like. One or more of the devices in the smart home environment need not physically be within the structure. For example, the controller 1030 which may receive input from the sensors 1010 and 1020 may be located outside of the structure.

The structure of the smart home environment may include a plurality of rooms, separated at least partly from each other via walls. The walls can include interior walls or exterior walls. Each room can further include a floor and a ceiling. Devices of the smart home environment, such as the sensors 1010 and 1020, may be mounted on, integrated with and/or supported by a wall, floor, or ceiling of the structure.

The smart home environment including the sensor network shown in FIG. 10A may include a plurality of devices, including intelligent, multi-sensing, network-connected devices, that can integrate seamlessly with each other and/or with a central server or a cloud-computing system (e.g., controller 1030 and/or remote system 1040) to provide home-security and smart home features. The smart home environment may include one or more intelligent, multi-sensing, network-connected thermostats (e.g., "smart thermostats"), one or more intelligent, network-connected, multi-sensing hazard detection units (e.g., "smart hazard detectors"), and one or more intelligent, multi-sensing, network-connected entryway interface devices (e.g., "smart doorbells"). The smart hazard detectors, smart thermostats, and smart doorbells may be the sensors 1010 and 1020 shown in FIG. 10A.

For example, a smart thermostat may detect ambient climate characteristics (e.g., temperature and/or humidity) and may accordingly control an HVAC (heating, ventilating, and air conditioning) system of the structure. For example, the ambient climate characteristics may be detected by sensors 1010 and 1020 shown in FIG. 10A, and the controller 1030 may control the HVAC system (not shown) of the structure.

As another example, a smart hazard detector may detect the presence of a hazardous substance or a substance indicative of a hazardous substance (e.g., smoke, fire, or carbon monoxide). For example, smoke, fire, and/or carbon monoxide may be detected by sensors 1010 and 1020 shown in FIG. 10A, and the controller 1030 may control an alarm system to provide a visual and/or audible alarm to the user of the smart home environment.

As another example, a smart doorbell may control doorbell functionality, detect a subject's approach to or departure from a location (e.g., an outer door to the structure), and announce a subject's approach or departure from the structure via audible and/or visual message that is output by a speaker and/or a display coupled to, for example, the controller 1030.

In some embodiments, the smart home environment of the sensor network shown in FIG. 10A may include one or more intelligent, multi-sensing, network-connected wall switches (e.g., "smart wall switches"), one or more intelligent, multi-sensing, network-connected wall plug interfaces (e.g., "smart wall plugs"). The smart wall switches and/or smart wall plugs may be or include one or more of the sensors 1010 and 1020 shown in FIG. 10A. A smart wall switch may detect ambient lighting conditions, and control a power and/or dim state of one or more lights. For example, a sensor such as sensors 1010 and 1020, may detect ambient lighting conditions, and a device such as the controller 1030 may control the power to one or more lights (not shown) in the smart home environment. Smart wall switches may also control a power state or speed of a fan, such as a ceiling fan. For example, sensors 1010 and 1020 may detect the power and/or speed of a fan, and the controller 1030 may adjust the power and/or speed of the fan, accordingly. Smart wall plugs may control supply of power to one or more wall plugs (e.g., such that power is not supplied to the plug if nobody is detected to be within the smart home environment). For example, one of the smart wall plugs may control supply of power to a lamp (not shown).

In embodiments of the disclosed subject matter, a smart home environment may include one or more intelligent, multi-sensing, network-connected entry detectors (e.g., "smart entry detectors"). Such detectors may be or include one or more of the sensors 1010 and 1020 shown in FIG. 10A. The illustrated smart entry detectors (e.g., sensors 1010 and 1020) may be disposed at one or more windows, doors, and other entry points of the smart home environment for detecting when a window, door, or other entry point is opened, broken, breached, and/or compromised. The smart entry detectors may generate a corresponding signal to be provided to the controller 1030 and/or the remote system 1040 when a window or door is opened, closed, breached, and/or compromised. In some embodiments of the disclosed subject matter, the alarm system, which may be included with controller 1030 and/or coupled to the network 1000 may not arm unless all smart entry detectors (e.g., sensors 1010 and 1020) indicate that all doors, windows, entryways, and the like are closed and/or that all smart entry detectors are armed.

The smart home environment of the sensor network shown in FIG. 10A can include one or more intelligent, multi-sensing, network-connected doorknobs (e.g., "smart doorknob"). For example, the sensors 1010 and 1020 may be coupled to a doorknob of a door (e.g., doorknobs located on external doors of the structure of the smart home environment). However, it should be appreciated that smart doorknobs can be provided on external and/or internal doors of the smart home environment.

The smart thermostats, the smart hazard detectors, the smart doorbells, the smart wall switches, the smart wall plugs, the smart entry detectors, the smart doorknobs, the keypads, and other devices of a smart home environment (e.g., as illustrated as sensors 1010 and 1020 of FIG. 10A) can be communicatively coupled to each other via the network 1000, and to the controller 1030 and/or remote system 1040 to provide security, safety, and/or comfort for the smart home environment. Alternatively or in addition, each of the devices of the smart home environment may provide data that can be used to determine an occupancy and/or physical status of a premises, as well as data that may be used to determine an appropriate recipient of a notification, as previously disclosed herein.

A user can interact with one or more of the network-connected smart devices (e.g., via the network 1000). For example, a user can communicate with one or more of the network-connected smart devices using a computer (e.g., a desktop computer, laptop computer, tablet, or the like) or other portable electronic device (e.g., a smartphone, a tablet, a key FOB, or the like). A webpage or application can be configured to receive communications from the user and control the one or more of the network-connected smart devices based on the communications and/or to present information about the device's operation to the user. For example, the user can view, arm or disarm the security system of the home.

One or more users can control one or more of the network-connected smart devices in the smart home environment using a network-connected computer or portable electronic device. In some examples, some or all of the users (e.g., individuals who live in the home) can register their mobile device and/or key FOBs with the smart home environment (e.g., with the controller 1030). Such registration can be made at a central server (e.g., the controller 1030 and/or the remote system 1040) to authenticate the user and/or the electronic device as being associated with the smart home environment, and to provide permission to the user to use the electronic device to control the network-connected smart devices and systems of the smart home environment. A user can use their registered electronic device to remotely control the network-connected smart devices and systems of the smart home environment, such as when the occupant is at work or on vacation. The user may also use their registered electronic device to control the network-connected smart devices when the user is located inside the smart home environment.

Alternatively, or in addition to registering electronic devices, the smart home environment may make inferences about which individuals live in the home (occupants) and are therefore users and which electronic devices are associated with those individuals. As such, the smart home environment may "learn" who is a user (e.g., an authorized user) and permit the electronic devices associated with those individuals to control the network-connected smart devices of the smart home environment (e.g., devices communicatively coupled to the network 1000) in some embodiments, including sensors used by or within the smart home environment. Various types of notices and other information may be provided to users via messages sent to one or more user electronic devices. For example, the messages can be sent via email, short message service (SMS), multimedia messaging service (MMS), unstructured supplementary service data (USSD), as well as any other type of messaging services and/or communication protocols. As previously described, such notices may be generated in response to specific determinations of the occupancy and/or physical status of a premises, or they may be sent for other reasons as disclosed herein.

A smart home environment may include communication with devices outside of the smart home environment but within a proximate geographical range of the home. For example, the smart home environment may include an outdoor lighting system (not shown) that communicates information through the communication network 1000 or directly to a central server or cloud-computing system (e.g., controller 1030 and/or remote system 1040) regarding detected movement and/or presence of people, animals, and any other objects and receives back commands for controlling the lighting accordingly.

The controller 1030 and/or remote system 1040 can control the outdoor lighting system based on information received from the other network-connected smart devices in the smart home environment. For example, in the event that any of the network-connected smart devices, such as smart wall plugs located outdoors, detect movement at nighttime, the controller 1030 and/or remote system 1040 can activate the outdoor lighting system and/or other lights in the smart home environment.

In some configurations, a remote system 1040 may aggregate data from multiple locations, such as multiple buildings, multi-resident buildings, individual residences within a neighborhood, multiple neighborhoods, and the like. In general, multiple sensor/controller systems 1050 and 1060 as shown FIG. 10B may provide information to the remote system 1040. The systems 1050 and 1060 may provide data directly from one or more sensors as previously described, or the data may be aggregated and/or analyzed by local controllers such as the controller 1030, which then communicates with the remote system 1040. The remote system may aggregate and analyze the data from multiple locations, and may provide aggregate results to each location. For example, the remote system 1040 may examine larger regions for common sensor data or trends in sensor data, and provide information on the identified commonality or environmental data trends to each local system 1050 and 1060. Aggregated data may be used to generate appropriate notices and/or determine appropriate recipients for such notices as disclosed herein. For example, the remote system 1040 may determine that the most common user response to a notification that a garage door has been left open while a security component of the smart home environment is in an armed state, is that the user returns to the premises and closes the garage door. Individual smart home systems and/or controllers as previously disclosed may receive such data from the remote system and, in response, set a default action of closing the garage door when the system determines that an armed state has been set and the garage door has been left open for more than a minimum threshold of time. The data provided to the individual systems may be only aggregate data, i.e., such that no individual information about any one other smart home environment or type of smart home environment is provided to any other. As another example, the remote system may receive data from multiple premises in a particular geographic region, indicating that it is raining in the region, and that the rain is moving east (based on the times at which the data indicating rainfall is received from different premises). In response, the remote system may provide an indication to premises further to the east that rain may be expected. In response, notifications may be provided to occupants of the individual premises that rain is expected, that particular windows should be closed, or the like. In some configurations users may be provided with the option of receiving such aggregated data, and/or with the option of providing anonymous data to a remote system for use in such aggregation. In some configurations, aggregated data also may be provided as "historical" data as previously disclosed. Such data may be used by a remote system and/or by individual smart home environments to identify trends, predict physical statuses of a premises, and the like.

In situations in which the systems discussed here collect personal information about users, or may make use of personal information, the users may be provided with an opportunity to control whether programs or features collect user information (e.g., information about a user's social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, specific information about a user's residence may be treated so that no personally identifiable information can be determined for the user, or a user's geographic location may be generalized where location information is obtained (such as to a city, ZIP code, or state level), so that a particular location of a user cannot be determined. As another example, systems disclosed herein may allow a user to restrict the information collected by those systems to applications specific to the user, such as by disabling or limiting the extent to which such information is aggregated or used in analysis with other information from other users. Thus, the user may have control over how information is collected about the user and used by a system as disclosed herein.

Figure 11:
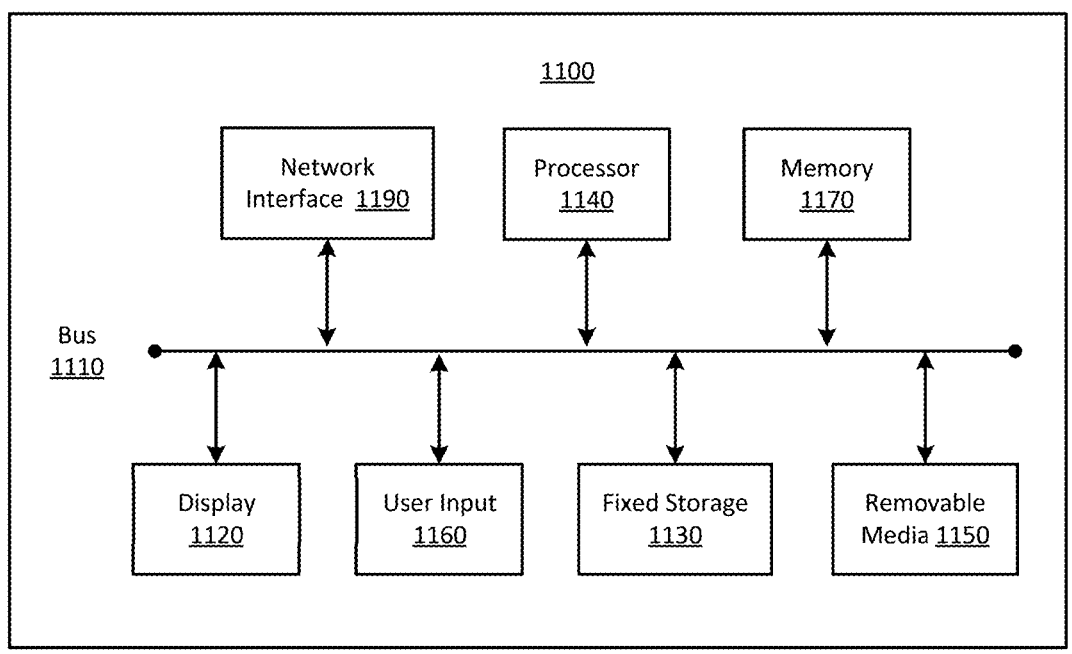
FIG. 11 shows a computing device according to an implementation of the disclosed subject matter.

Embodiments of the presently disclosed subject matter may be implemented in and used with a variety of computing devices. FIG. 11 is an example of a computing device 1100 suitable for implementing embodiments of the disclosed subject matter. For example, the device 1100 may be used to implement a controller, a device including sensors as disclosed herein, or the like. Alternatively or in addition, the device 1100 may be, for example, a desktop or laptop computer, or a mobile computing device such as a smart phone, tablet, or the like. The device 1100 may include a bus 1110 which interconnects major components of the computer 1100, such as a central processor 1140, a memory 1170 such as Random Access Memory (RAM), Read Only Memory (ROM), flash RAM, or the like, a user display 1120 such as a display screen, a user input interface 1160, which may include one or more controllers and associated user input devices such as a keyboard, mouse, touch screen, and the like, a fixed storage 1130 such as a hard drive, flash storage, and the like, a removable media component 1150 operative to control and receive an optical disk, flash drive, and the like, and a network interface 1190 operable to communicate with one or more remote devices via a suitable network connection.

The bus 1110 allows data communication between the central processor 1140 and one or more memory components 1150 and 1170, which may include RAM, ROM, and other memory, as previously noted. Applications resident with the computer 1100 are generally stored on and accessed via a computer readable storage medium.

The fixed storage 1130 may be integral with the computer 1100 or may be separate and accessed through other interfaces. The network interface 1190 may provide a direct connection to a remote server via a wired or wireless connection. The network interface 1190 may provide such connection using any suitable technique and protocol as will be readily understood by one of skill in the art, including digital cellular telephone, Wi-Fi, Bluetooth®, near-field, and the like. For example, the network interface 1190 may allow the device to communicate with other computers via one or more local, wide-area, or other communication networks, as described in further detail herein.

Figure 12:
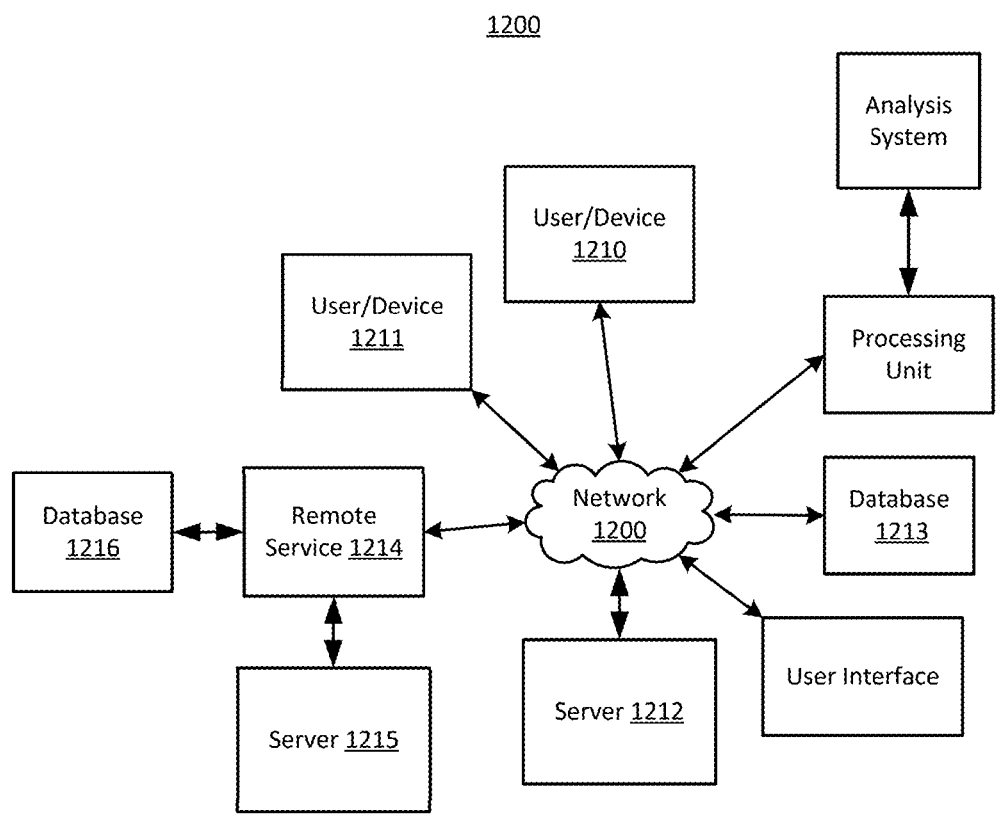
FIG. 12 shows a networked arrangement according to an implementation of the disclosed subject matter.

FIG. 12 shows an example network arrangement according to an embodiment of the disclosed subject matter. One or more devices 1210 and 1211, such as local computers, smart phones, tablet computing devices, and the like may connect to other devices via one or more networks 1200. Each device may be a computing device as previously described. The network may be a local network, wide-area network, the Internet, or any other suitable communication network or networks, and may be implemented on any suitable platform including wired and/or wireless networks. The devices may communicate with one or more remote devices, such as servers 1212 and/or databases 1213. The remote devices may be directly accessible by the devices 1210 and 1211, or one or more other devices may provide intermediary access such as where a server 1212 provides access to resources stored in a database 1213. The devices 1210 and 1211 also may access remote platforms 1214 or services provided by remote platforms 1214 such as cloud computing arrangements and services. The remote platform 1214 may include one or more servers 1215 and/or databases 1216.

Various embodiments of the presently disclosed subject matter may include or be embodied in the form of computer-implemented processes and apparatuses for practicing those processes. Embodiments also may be embodied in the form of a computer program product having computer program code containing instructions embodied in non-transitory and/or tangible media, such as hard drives, USB (universal serial bus) drives, or any other machine readable storage medium, such that when the computer program code is loaded into and executed by a computer, the computer becomes an apparatus for practicing embodiments of the disclosed subject matter. When implemented on a general-purpose microprocessor, the computer program code may configure the microprocessor to become a special-purpose device, such as by creation of specific logic circuits as specified by the instructions.

Embodiments may be implemented using hardware that may include a processor, such as a general purpose microprocessor and/or an Application Specific Integrated Circuit (ASIC) that embodies all or part of the techniques according to embodiments of the disclosed subject matter in hardware and/or firmware. The processor may be coupled to memory, such as RAM, ROM, flash memory, a hard disk or any other device capable of storing electronic information. The memory may store instructions adapted to be executed by the processor to perform the techniques according to embodiments of the disclosed subject matter.

The foregoing description, for purpose of explanation, has been described with reference to specific embodiments. However, the illustrative discussions above are not intended to be exhaustive or to limit embodiments of the disclosed subject matter to the precise forms disclosed. Many modifications and variations are possible in view of the above teachings. The embodiments were chosen and described in order to explain the principles of embodiments of the disclosed subject matter and their practical applications, to thereby enable others skilled in the art to utilize those embodiments as well as various embodiments with various modifications as may be suited to the particular use contemplated.

The invention claimed is:

1. A method for determining an occurrence of a sleep disorder, the method comprising:
   emitting a first emission sequence of radiation toward a subject;
   capturing a first reflected sequence of radiation reflected from the subject;
   comparing the first emission sequence to the first reflected sequence;
   determining a sequence of variations based on a comparison of the first emission sequence to the first reflected sequence;
   comparing the sequence of variations to a sleep profile of the subject;
   determining, based on a comparison of the sequence of variations to the sleep profile, the subject has exhibited a sleep behavior;
   in response to a determination that the subject has exhibited the sleep behavior, capturing a second reflected sequence of radiation reflected from the subject;
   determining, from the second reflected sequence of radiation, a breathing rate of the subject;
   comparing the breathing rate to a breathing rate associated with sleep disorder data;
   determining, from the second reflected sequence of radiation, a portion of the second reflected sequence of radiation reflected from a face of the subject;
   receiving, from a sensor, information about a temperature in a vicinity of the subject;
   filtering, based on the temperature, the portion of the second reflected sequence by reducing at least one energy peak of the portion of the second reflected sequence of radiation to produce a filtered portion of the second reflected sequence;
   determining, using the filtered portion of the second reflected sequence, a heart rate of the subject;
   comparing the heart rate to a heart rate associated with the sleep disorder data;
   determining, in response to:
   a result of a comparison between the breathing rate and the breathing rate associated with the sleep disorder being within a first threshold; or
   a result of a comparison between the heart rate and the heart rate associated with the sleep disorder data being within a second threshold, the occurrence of the sleep disorder; and
   causing, in response to the occurrence of the sleep disorder, a notice about the occurrence of the sleep disorder to be provided.

2. The method of claim 1, wherein the sleep disorder data are stored in the sleep profile and the providing the notice comprises providing the notice to a home automation system.

3. The method of claim 1, wherein the first emission sequence, the first reflected sequence, and the second reflected sequence each comprises infrared radiation.

4. The method of claim 1, wherein the sequence of variations comprises a first sequence of variations and the sleep profile comprises a second sequence of variations that is correlated to the subject exhibiting the sleep behavior.

5. The method of claim 1, wherein:
   the sequence of variations comprises a first sequence of variations;
   the sleep profile comprises a second sequence of variations that is correlated to the subject exhibiting the sleep behavior; and
   the sleep behavior comprises movements of the subject consistent with the subject moving into a sleeping position.

6. The method of claim 1, wherein the first reflected sequence comprises the second reflected sequence.

7. The method of claim 1, wherein the determining the breathing rate of the subject comprises:
   detecting a first variation in a quantity of radiation in the second reflected sequence;
   determining that the subject has entered a sleep stage based on the first variation in the quantity of radiation in the second reflected sequence;
   detecting a second variation in the quantity of radiation in the second reflected sequence; and
   determining the breathing rate based on the second variation in the quantity.

8. The method of claim 1, wherein the determining the heart rate comprises detecting a variation in a quantity of radiation in the second reflected sequence reflected from the face of the subject.

9. A system for determining an occurrence of a sleep disorder, the system comprising:
   a device comprising a radiation emission component and a radiation capture component; and
   a processor configured to be in communication with the device and configured to execute instructions for:
   emitting, from the radiation emission component, a first emission sequence of radiation toward a subject;
   capturing, at the radiation capture component, a first reflected sequence of radiation reflected from the subject;
   comparing the first emission sequence to the first reflected sequence;

determining a sequence of variations based on a comparison of the first emission sequence to the first reflected sequence;
comparing the sequence of variations to a sleep profile of the subject;
determining, based on a comparison of the sequence of variations to the sleep profile, that the subject has exhibited a sleep behavior;
in response to a determination that the subject has exhibited the sleep behavior, capturing, at the radiation capture component, a second reflected sequence of radiation;
determining, from the second reflected sequence of radiation, a breathing rate of the subject;
comparing the breathing rate to a breathing rate associated with sleep disorder data;
determining, from the second reflected sequence of radiation, a portion of the second reflected sequence of radiation reflected from a face of the subject;
receiving, from a sensor, information about a temperature in a vicinity of the subject;
filtering, based on the temperature, the portion of the second reflected sequence by reducing at least one energy peak of the portion of the second reflected sequence of radiation to produce a filtered portion of the second reflected sequence;
determining, using the filtered portion of the second reflected sequence, a heart rate of the subject;
comparing the heart rate to a heart rate associated with the sleep disorder data;
determining, in response to:
a result of a comparison between the breathing rate and the breathing rate associated with the sleep disorder being within a first threshold; or
a result of a comparison between the heart rate and the heart rate associated with the sleep disorder data being within a second threshold, the occurrence of the sleep disorder; and
causing, in response to the occurrence of the sleep disorder, a notice about the occurrence of the sleep disorder to be provided.

10. The system of claim 9, wherein:
the first reflected sequence of radiation comprises a first reflected sequence of patterns of radiation; and
the sequence of variations comprises a sequence of variations of patterns of radiation.

11. The system of claim 9, wherein the first emission sequence, the first reflected sequence, and the second reflected sequence each comprises infrared radiation.

12. The system of claim 9, wherein the processor is further configured to execute instructions for:
prior to the capturing the second reflected sequence, emitting, from the radiation emission component, a second emission sequence of radiation toward the subject.

13. The system of claim 9, wherein:
the radiation emission component comprises a plurality of radiation emission components;
the first reflected sequence comprises a first reflected sequence of patterns of radiation emitted from the plurality of radiation emission components; and
the second reflected sequence comprises a second reflected sequence of patterns of radiation emitted from no more than one radiation emission component of the plurality of radiation emission components.

14. The system of claim 9, wherein:
the radiation emission component comprises a plurality of radiation emission components;
the plurality of radiation emission components are configured to emit a first emission sequence of patterns of radiation; and
each pattern of the first emission sequence of patterns of radiation comprises an array comprising a plurality of elements.

15. A non-transitory computer readable medium storing computer code for controlling a processor to cause the processor to determine an occurrence of a sleep disorder, the computer code including instructions to cause the processor to:
compare a first emission sequence of radiation to a first reflected sequence of radiation, the first emission sequence having been emitted toward a subject, the first reflected sequence having been captured after having been reflected from the subject;
determine a sequence of variations based on a comparison of the first emission sequence to the first reflected sequence;
compare the sequence of variations to a sleep profile of the subject;
determine, based on a comparison of the sequence of variations to the sleep profile, that the subject has exhibited a sleep behavior;
in response to a determination that the subject has exhibited the sleep behavior, determine, from a second reflected sequence of radiation, a breathing rate of the subject, the second reflected sequence having been captured;
compare the breathing rate to a breathing rate associated with sleep disorder data;
determine, from the second reflected sequence of radiation, a portion of the second reflected sequence of radiation reflected from a face of the subject;
receiving, from a sensor, information about a temperature in a vicinity of the subject;
filtering, based on the temperature, the portion of the second reflected sequence by reducing at least one energy peak of the portion of the second reflected sequence of radiation to produce a filtered portion of the second reflected sequence;
determining, using the filtered portion of the second reflected sequence, a heart rate of the subject;
compare the heart rate to a heart rate associated with the sleep disorder data;
determine, in response to:
a result of a comparison between the breathing rate and the breathing rate associated with the sleep disorder being within a first threshold; or
a result of a comparison between the heart rate and the heart rate associated with the sleep disorder data being within a second threshold, the occurrence of the sleep disorder; and
cause, in response to the occurrence of the sleep disorder, a notice about the occurrence of the sleep disorder to be provided.

16. The non-transitory computer readable medium of claim 15, wherein the first emission sequence, the first reflected sequence, and the second reflected sequence each comprises infrared radiation.

17. The non-transitory computer readable medium of claim 15, wherein the second reflected sequence is distinct from the first reflected sequence.

18. The non-transitory computer readable medium of claim 15, wherein:
the subject comprises a child;
the instructions further cause the processor to determine the sleep disorder based on the comparison of the sequence of variations to the sleep profile; and
the sleep disorder comprises an awake child.

19. The system of claim 9, wherein the determining the heart rate of the subject comprises:
analyzing the portion of the second reflected sequence of radiation to detect a periodically changing wavelength;
determining energy peaks of the periodically changing wavelength;
determining a rate of the energy peaks; and
determining the heart rate of the subject to correspond to the rate of the energy peaks.

20. The system of claim 9, wherein the processor is further configured to execute instructions for recording, to a memory, the heart rate of the subject, wherein the comparing the heart rate to the heart rate associated with the sleep disorder data occurs periodically.

21. The system of claim 9, wherein the sleep disorder data are stored in the sleep profile.

22. The system of claim 9, wherein the providing the notice comprises providing the notice to a home automation system.

23. The system of claim 9, wherein the device is incorporated into an item of furniture.

24. The system of claim 23, wherein the furniture comprises at least one of a bed, a night stand, a dresser, a lamp, a crib, a mobile configured to be positioned over the crib, a television, a video monitor, or an audio device.

25. The system of claim 9, wherein the device is configured to be attached to at least one of an overhead fan, a lighting fixture, a ceiling, a pillar, a wall surface, or a molding.

26. The system of claim 9, wherein the device is configured to be coupled to a network in communication with a home automation system or a home monitoring hub.

27. The system of claim 9, wherein the radiation emission component comprises at least one of a light emitting diode, a laser, or a lens-focused light source.

28. The system of claim 9, wherein the radiation capture component comprises at least one of an image sensor, a photodiode, a charge-coupled device, a complementary metal-oxide-semiconductor device, a red green blue imaging camera, a red green blue-depth imaging camera, or an infrared imaging sensor.

29. The system of claim 9, wherein the determining the breathing rate of the subject comprises:
determining dominant frequencies in the second reflected sequence of radiation;
determining energy peaks in the dominant frequencies;
determining a rate of the energy peaks; and
determining the breathing rate of the subject to correspond to the rate of the energy peaks.

30. The system of claim 9, wherein the processor is further configured to execute instructions for recording, to a memory, the breathing rate of the subject, wherein the comparing the breathing rate to the breathing rate associated with the sleep disorder data comprises comparing, periodically, the breathing rate to the breathing rate associated with the sleep disorder data.

* * * * *